(12) United States Patent
Oertling et al.

(10) Patent No.: US 9,446,267 B2
(45) Date of Patent: Sep. 20, 2016

(54) PRODUCTS COMPRISING A FLAVORING AGENT COMPOSITION

(75) Inventors: Heiko Oertling, Holzminden (DE); Hubert Loges, Höxter (DE); Arnold Machinek, Holzminden (DE); Ulrike Simchen, Holzminden (DE); Horst Surburg, Holzminden (DE)

(73) Assignee: SYMRISE AG, Holzminden (DE)

( * ) Notice: Subject to any disclaimer, the term of this patent is extended or adjusted under 35 U.S.C. 154(b) by 18 days.

(21) Appl. No.: 12/898,893

(22) Filed: Oct. 6, 2010

(65) Prior Publication Data
US 2011/0081303 A1 Apr. 7, 2011

Related U.S. Application Data

(60) Provisional application No. 61/249,133, filed on Oct. 6, 2009.

(51) Int. Cl.
| A61K 8/42 | (2006.01) |
| A61Q 11/00 | (2006.01) |
| A61K 8/02 | (2006.01) |
| A61K 8/11 | (2006.01) |
| A61K 8/34 | (2006.01) |
| A61K 8/35 | (2006.01) |
| A61K 8/36 | (2006.01) |

(52) U.S. Cl.
CPC .......... *A61Q 11/00* (2013.01); *A61K 8/0216* (2013.01); *A61K 8/0241* (2013.01); *A61K 8/11* (2013.01); *A61K 8/347* (2013.01); *A61K 8/35* (2013.01); *A61K 8/36* (2013.01); *A61K 2800/244* (2013.01)

(58) Field of Classification Search
USPC ................ 424/48; 426/3; 514/548; 560/188
See application file for complete search history.

(56) References Cited

U.S. PATENT DOCUMENTS

| 4,150,052 | A | 4/1979 | Watson et al. |
| 4,178,459 | A | 12/1979 | Watson et al. |
| 5,002,791 | A | 3/1991 | Knebl |
| 5,009,893 | A | 4/1991 | Cherukuri et al. |
| 5,372,824 | A | 12/1994 | Record et al. |
| 5,451,404 | A | 9/1995 | Furman |
| 5,458,894 | A | 10/1995 | Knebl et al. |
| 5,601,858 | A | 2/1997 | Mansukhani et al. |
| 5,695,746 | A | 12/1997 | Garlick, Jr. et al. |
| 6,432,441 | B1 | 8/2002 | Bealin-Kelly et al. |
| 6,627,233 | B1 | 9/2003 | Wolf et al. |
| 2002/0188019 | A1 | 12/2002 | Ley et al. |
| 2004/0241312 | A1 | 12/2004 | Gatfield et al. |
| 2005/0187211 | A1 | 8/2005 | Wei |
| 2007/0053834 | A1 | 3/2007 | Wei |
| 2007/0148283 | A1* | 6/2007 | Harvey et al. ............ 426/3 |
| 2007/0155755 | A1 | 7/2007 | Wei |
| 2007/0233026 | A1 | 10/2007 | Roe et al. |
| 2009/0054520 | A1 | 2/2009 | Surburg et al. |

(Continued)

FOREIGN PATENT DOCUMENTS

| DE | 2503555 A1 | 8/1975 |
| DE | 10351422 A1 | 6/2005 |

(Continued)

OTHER PUBLICATIONS

International Search Report, European Application No. 09172357.7, dated Mar. 26, 2010.

(Continued)

*Primary Examiner* — Walter Webb
(74) *Attorney, Agent, or Firm* — Polsinelli PC

(57) ABSTRACT

The present invention primarily concerns teeth cleaning compounds containing menthol for use with a toothbrush, preferably tooth pastes, tooth crèmes, tooth cleaning gels or tooth powders. Such a tooth cleaning compound according to the invention contains menthol and a quantity, for masking the bitterness of the menthol, of menthane carboxylic acid-N-(4-methoxyphenyl)-amide (WS-12) of the following formula (Ia), in particular of the following formula (Ib), i.e. L-menthane carboxylic acid-N-(4-methoxyphenyl)-amide.

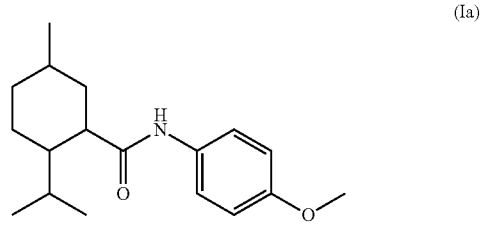

(Ia)

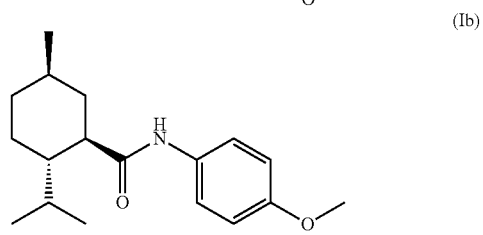

(Ib)

The present invention also concerns the use of menthane carboxylic acid-N-(4-methoxyphenyl)-amide (WS-12) of the formulas (Ia) or (preferably) (Ib) to mask the bitter taste of menthol in a teeth cleaning compound.

The present invention also concerns a method for dissolving menthane carboxylic acid-N-(4-methoxyphenyl)-amide (WS-12) in a teeth cleaning compound and a method for masking the bitterness of menthol in a teeth cleaning compound.

16 Claims, 1 Drawing Sheet

(56) References Cited

U.S. PATENT DOCUMENTS

2009/0098173 A1 4/2009 Robinson et al.
2009/0148938 A1 6/2009 Gravina et al.

FOREIGN PATENT DOCUMENTS

| EP | 2033688 A2 | 3/2009 |
|---|---|---|
| EP | 2068150 A1 | 6/2009 |
| GB | 1351761 A | 5/1974 |
| GB | 1351762 A | 5/1974 |
| GB | 1457671 A | 12/1976 |
| WO | WO-9617524 A1 | 6/1996 |
| WO | WO-2004000787 A2 | 12/2003 |
| WO | WO-2004026840 A1 | 4/2004 |
| WO | WO-2004050069 A1 | 6/2004 |
| WO | WO-2004078302 A1 | 9/2004 |
| WO | WO-2005002582 A2 | 1/2005 |
| WO | WO-2005020897 A2 | 3/2005 |
| WO | WO-2005096841 A1 | 10/2005 |
| WO | WO-2006024587 A1 | 3/2006 |
| WO | WO-2006058893 A2 | 6/2006 |
| WO | WO-2006103401 A2 | 10/2006 |
| WO | WO-2006106023 A1 | 10/2006 |
| WO | WO-2006116436 A1 | 11/2006 |
| WO | WO-2007003527 A1 | 1/2007 |
| WO | WO-2007014879 A1 | 2/2007 |
| WO | WO-2008015403 A1 | 2/2008 |
| WO | WO-2008138162 A1 | 11/2008 |

OTHER PUBLICATIONS

Office Action, European Application No. 09172357.7, dated Dec. 3, 2010.
Watson, H.R., et al., "New compounds with the menthol cooling effect," J. Soc. Cosmet. Chem., 29, 185-200 (1978).
Beck, B., et al., "Prospects for prostate cancer imaging and therapy using high-affinity TRPM8 activators," Cell Calcium 41 (2007) 285-294.
Bödding, M., et al., "Characterisation of TRPM8 as a pharmacophore receptor," Cell Calcium 42 (2007) 618-628.
Ma, S., "Menthol Derivative WS-12 Selectively Activates Transient Receptor Potential Melastatin-8 (TRPM8) Ion Channels," Pak. J. Pharm. Sci., vol. 21, No. 4, Oct. 2008, pp. 370-378.
Erman, M., "New Developments in Physiological Cooling Agents," Perfumer & Flavorist, vol. 32(10), 20-35 (2007).
Rowe, D. J., Chemistry and Technology of Flavors and Fragrances, Blackwell Publishing Ltd, Oxford 2005, p. 212-222.
Furrer, S. M., et al., "New Developments in the Chemistry of Cooling Compounds," Chem. Percept. (2008) 1:119-126.

* cited by examiner

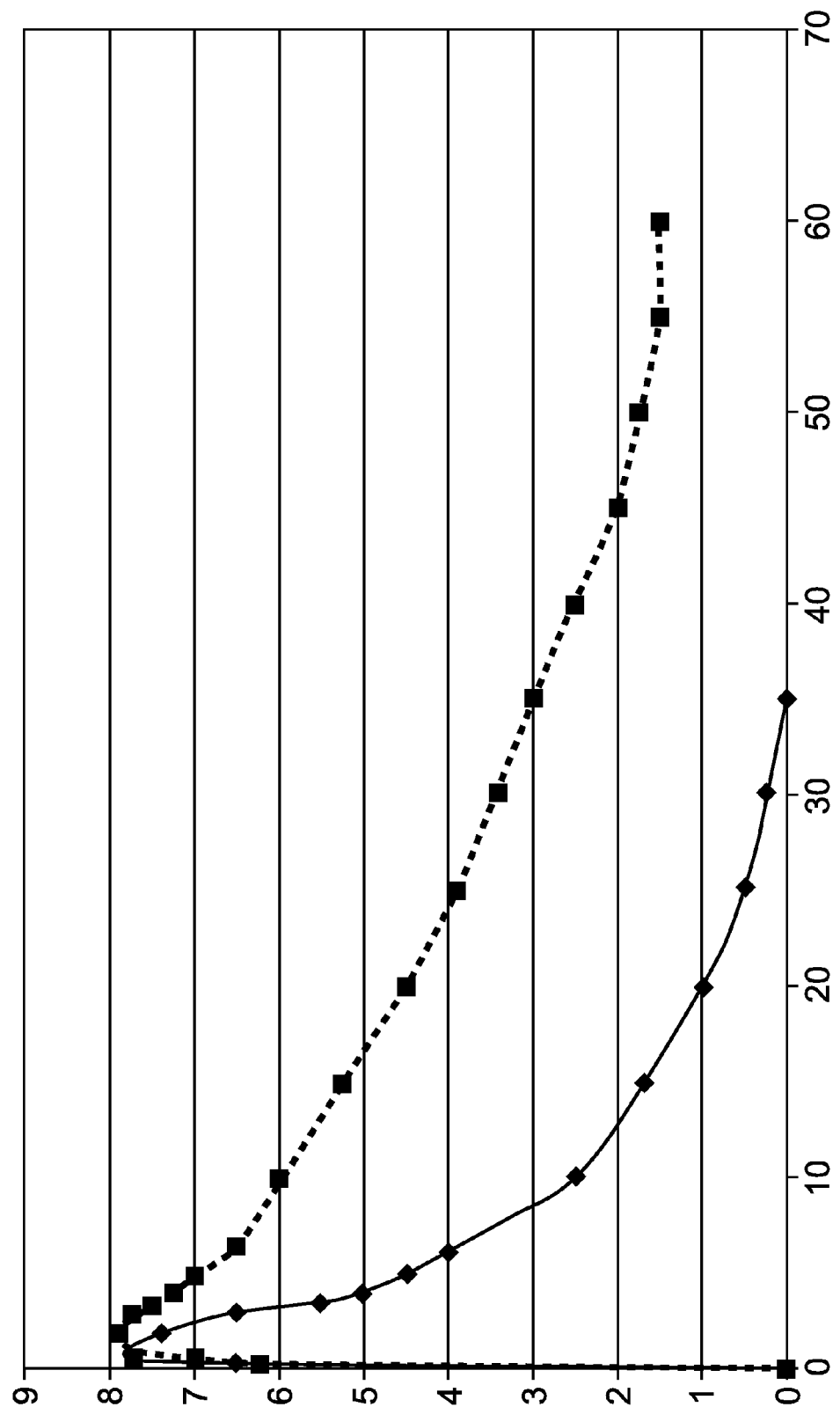

PRODUCTS COMPRISING A FLAVORING AGENT COMPOSITION

CROSS-REFERENCE TO RELATED APPLICATIONS

This application claims priority under 35 U.S.C. §119(e) to U.S. provisional application No. 61/249,133, filed Oct. 6, 2009, the entire contents of which is hereby incorporated by reference.

The present invention primarily concerns teeth cleaning compounds containing menthol for use with a toothbrush, preferably tooth pastes, tooth crèmes, tooth cleaning gels or tooth powders. Such a teeth cleaning compound according to the invention contains menthol and a quantity, for masking the bitterness of the menthol, of menthane carboxylic acid-N-(4-methoxyphenyl)-amide (WS-12) of the following formula (Ia), in particular of the following formula (Ib), i.e. L-menthane carboxylic acid-N-(4-methoxyphenyl)-amide.

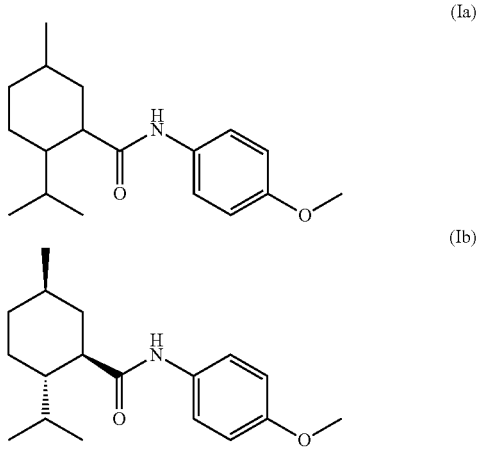

The present invention also concerns the use of menthane carboxylic acid-N-(4-methoxyphenyl)-amide (WS-12) of formulas (Ia) or (preferably) (Ib) to mask the bitter taste of menthol in a teeth cleaning compound.

The present invention also concerns a method for dissolving menthane carboxylic acid-N-(4-methoxyphenyl)-amide (WS-12) in a teeth cleaning compound and a method for masking the bitterness of menthol in a teeth cleaning compound.

Details of the abovementioned aspects of the present invention and further aspects of the invention, in particular particularly preferred embodiments, can be found in the following description, the examples and the attached claims.

Teeth cleaning compounds currently available in the market for use with a toothbrush, in particular toothpastes, tooth crèmes, tooth cleaning gels and tooth powders, these days usually contain a relatively large number of agents, e.g. to act against caries, dental plaque, gingivitis, dental neck sensitivity, dental calculus formation, bad breath, and so on. These agents are often accompanied by highly unpleasant taste impressions, so that the said teeth cleaning compounds are normally highly flavored. Substances such as triclosan, potassium or zinc citrate, tin chloride, tin fluoride, amine fluoride, or cetylpyridinium chloride can for example lead to salty, metallic, acrid, bitter, astringent, anaesthetizing, burning, soapy or stale taste notes.

In order to cover up or mask the extremely negatively perceived taste notes of the agents used in the teeth cleaning compounds (i.e. to reduce or to minimize them) and at the same time to provide the user with a pleasant feeling of freshness, in recent years the proportion of flavoring used in a teeth cleaning compound has been increased from previously approximately 1 wt. % to approximately 1.2 to 1.3 wt. % today, and in some cases even 1.5 wt. % or more. The wt. % details refer here to the finished teeth cleaning compound. Within the flavoring components of a teeth cleaning compound the overall proportion of the menthol used in practice has been increased just as much as the proportion of menthol added (linearly) as an individual component. Previously the overall proportion of menthol was often 10-20 wt. %, in relation to the flavoring agent composition within a conventional teeth cleaning compound, while today overall quantities of menthol of approximately 40-50 wt. % are normal, in relation to the overall weight of the flavoring composition. The overall quantity of menthol here is the total of (a) menthol that has been added to the flavoring in the form of a formulation containing menthol and (b) menthol, which has been added (linearly) as an individual component. To sum up, therefore, in recent years the proportion of menthol in teeth cleaning compounds available in the market has increased by a factor of 4.

The continued increase over the years in the proportion of menthol in teeth cleaning compounds brings with it a number of advantages but also considerable disadvantages. Although an increased proportion of menthol, thanks to the greater sensation of freshness and coolness, is quite effective in covering up the abovementioned negative taste notes of the agents used in teeth cleaning compounds, the increasing quantities of menthol now being used are also accompanied by negative taste characteristics and, in particular in higher concentrations, this is often perceived as sharp and bitter. As a result there is a need to mask the taste notes caused by the menthol in teeth cleaning compounds.

In practice in many cases use is made in teeth cleaning compounds of anethole, which because of its sweet taste is able to reduce the sharpness and bitterness of the menthol. For its part, however, anethole has a strong aniseed taste, which is rejected by many consumers. Because of this strong and characteristic inherent taste, the presence of anethole in a teeth cleaning compound also restricts the use of further flavoring agents with other tastes, since the inherent taste of anethole is difficult to combine with other tastes to form a harmonious unit, in particular when used in higher concentrations. This appears to be particularly problematic inasmuch as there is increasing demand for new taste impressions of teeth cleaning compounds.

A primary object of the present invention was to indicate a teeth cleaning compound which, apart from the normal constituents such as for example cleaning granules, contains a flavoring composition that imparts a fresh and cool sensation, without providing a significant or troublesome sharp or bitter taste note.

Other considerations mean that in future the constitution of teeth cleaning compounds should preferably not completely dispense with the use of menthol in stated teeth cleaning compounds. A particular problem in connection with the present invention was therefore to indicate a teeth cleaning compound which, apart from the normal constituents such as for example cleaning granules, contains a flavoring composition containing menthol, wherein on the basis of measures to be specified, the menthol does indeed impart the desired sensation of freshness and coolness, but not the undesired taste of sharpness or bitterness.

Further (sub-)objects in connection with the invention will emerge from the following to statements, in particular when considering the stated advantages of teeth cleaning compounds according to the invention.

If one considers the above statements on the negative aspects of the agents normally used in teeth cleaning compounds (negative taste notes), of the menthol used to mask these negative taste notes (its own negative taste notes in higher concentrations) and finally of the anethole used to mask the negative taste notes of the menthol (strong inherent taste that limits the possibilities for variation when using other flavoring agents), then it can be established that in customary teeth cleaning compounds there is already a complex interplay between taste dependencies. This explains why in the market to date no convincing alternatives to the teeth cleaning compounds depicted above have been found.

The primary object stated above is achieved according to the invention by a teeth cleaning compound, preferably by a tooth paste, a tooth crèmes, a tooth cleaning gel or a tooth powder, for use with a toothbrush, containing the following components:
(i) cleaning granules
(ii) flavoring agent composition containing or consisting of:
  a) Menthol,
  b) a quantity of menthane carboxylic acid-N-(4-methoxyphenyl)-amide (WS-12) to mask the bitterness of the menthol, and
  c) one, two or more further flavoring agents, wherein the, a plurality or all of the further flavoring agents have a log-$K_{ow}$ value in the range of 1.5-5.

Surprisingly our own investigations have shown that menthane carboxylic acid-N-(4-methoxyphenyl)-amide (WS-12), preferably L-menthane carboxylic acid-N-(4-methoxyphenyl)-amide (see above formulas (Ia) and (Ib)) when used in a sufficient quantity is able to mask the bitterness of menthol in a flavoring agent composition of a teeth cleaning compound. Said investigations showed that quantity of WS-12 necessary for masking cannot readily be incorporated into a teeth cleaning compound. Menthane-3-carboxylic acid-N-(4-methoxyphenyl)-amide is a crystalline substance with a melting point of 177° C., which is relatively not readily soluble. In order to bring about the masking of the menthol to a sufficient extent, WS-12 must be dissolved in the flavoring agent composition of the teeth cleaning compound in a sufficient quantity. Our own preliminary investigations have shown that in certain conventional flavoring agent compositions the solubility of the WS-12 is so low that only an insufficient masking (reduction or decrease) in the negative taste impressions of the menthol can be achieved. Surprisingly, however, it transpires that in the presence of the component (ii) c) to be used according to the invention, i.e. one, two or more further flavoring agents, wherein the, a plurality or all of the further flavoring agents have a log-$K_{ow}$ value in the range of 1.5-5, the solubility of WS-12 is increased such that a quantity of WS-12 masking the bitterness of the menthol can be properly and durably incorporated into the teeth cleaning compound.

The result is a teeth cleaning compound according to the invention with a number of advantages, some of which are explained in detail below. In particular, however, it is a case of a teeth cleaning compound, in which despite the presence of (considerable quantities of) menthol, the bitterness of the menthol no longer has a troublesome effect, because it is masked by the simultaneous presence of WS-12. Therefore, the menthol can, for example in keeping with its original purpose, mask the negative taste impressions of the agents used in conventional teeth cleaning compounds, without the negative taste aspects of the menthol remaining disadvantageously.

Menthane carboxylic acid-N-(4-methoxyphenyl)-amide (WS-12) was first described as a possible cooling agent in U.S. Pat. No. 4,150,052.

In J. Soc. Cosmet. Chem. 1978, 29, 185-200 the results were presented of a study of approximately 1200 compounds, in which the compounds L-menthane carboxylic acid-N-ethyl amide (WS-3) and also L-menthane carboxylic acid-N-(4-methoxyphenyl)-amide (WS-12) were identified as cooling agents.

Menthane carboxylic acid-N-(4-methoxyphenyl)-amide (WS-12) has thus been known for a long time as a possible cooling agent, but has not to date been used in practice to an appreciable extent.

DE 2503555 describes a taste-enhancing effect of menthane carboxylic acid-N-(4-methoxyphenyl)-amide in coffee preparations, powdered tea and orange juice and GB 1351762 concerns the use of, inter alia, menthane carboxylic acid-N-(4-methoxyphenyl)-amide in tobacco products.

The synthesis of WS-12 is described in U.S. Pat. Nos. 4,178,459, 4,150,052 and GB 1351761.

The cooling effect of menthane carboxylic acid-N-(4-methoxyphenyl)-amide and in this connection its function of activating physiological cold receptor TRPM8 are described in WO 2005/020897 A2 (Dendreon Corporation) and WO 2005/002582 A2 (Genentech Inc.).

In EP 2 068 150 various cooling agents were investigated for their cooling effect. Here the relative cooling strengths compared with L-menthol were determined, with L-menthol being given a strength of 100. According to EP 2 068 150 the cooling strength of L-menthane carboxylic acid-N-ethyl amide (WS-3) and of L-menthane carboxylic acid-N-(4-methoxyphenyl)-amide (WS-12) was 150 in each case. At 400, however, $N^{\alpha}$-(L-menthane carbonyl)-glycine ethyl ester (WS-5) was rated as having a significantly stronger cooling effect.

In WO 2006/103401 A2 the cooling effect of menthane carboxylic acid-N-(4-methoxyphenyl)-amide when remaining on the upper lip for up to half an hour is described. The cooling effect is described as lower than WS-5. It is commented that this state of affairs is contrary to the trials on the TRPM8 cold receptor in which WS-12 demonstrates a stronger effect than WS-5.

The fact that menthane carboxylic acid-N-(4-methoxyphenyl)-amide is one of the strongest cooling substances on the cold receptor TRPM8, is also described in Cell Calcium (42) 2007, 618 and in Cell Calcium (41), 2007, 285 and in Pak. J. Pharm. Sci. Vol. 21, 4, 2008, 370.

In US 2005/0187211 A1 under the name 'CPS-112' the cooling duration of menthane carboxylic acid-N-(4-methoxyphenyl)-amide is given as under one hour on the philtrum fold (upper lip). In US 2007/0053834A1 the threshold value of WS-12 for a cold sensation on the tongue is described.

The solubility in water of menthane carboxylic acid-N-(4-methoxyphenyl)-amide is described in US 2007/0155755 A1.

The use of menthane carboxylic acid-N-(4-methoxyphenyl)-amide as a cooling substance on the skin (sensually perceptible signal) is described in US 2007/0233026 A1.

WO 2008/015403 A1 discloses the use of menthane carboxylic acid-N-(4-methoxyphenyl)-amide in a medicament for chronic pain.

WO 2008/138162 and EP 2 033 688, in the context of the invention described there in each case, also describe the use of menthane carboxylic acid-N-(4-methoxyphenyl)-amide as a possible cooling agent.

U.S. Pat. Nos. 5,009,893, 5,372,824 and WO 96/17524 disclose certain edible compositions (in particular chewing gum compositions), in which menthol and certain N-substituted amides of menthane-3-carboxylic acid are present. These compositions are to demonstrate a long-lasting perception of breath freshening without bitterness. A particularly suitable amide mentioned here is menthane-3-carboxylic acid-N-ethyl amide.

In our own investigations the use of menthane-3-carboxylic acid-N-ethyl amide, which was central to the considerations of the three patent specifications just discussed, proved to a large extent to be ineffective in teeth cleaning compounds. In particular, in our own investigations the addition of menthane-3-carboxylic acid-N-ethyl amide to a conventional teeth cleaning compound containing menthol did not lead to a significant reduction or masking of the bitterness or sharpness caused by menthol.

The ineffectiveness of menthane-3-carboxylic acid-N-ethyl amide in teeth cleaning compounds (and in particular in toothpaste) may be due to the difference in structure between the teeth cleaning compound and a chewing gum. Toothpastes are viscous suspensions, which rapidly become thin during teeth-cleaning through dilution with saliva. Normal viscosity values for toothpastes are in the range of 50-400 Pa s at 25° C.

Toothpastes according to the invention (as an example of a particularly preferred teeth cleaning compound) preferably have viscosity values in the range of 10-500 Pa s, preferably in the range of 50-450 Pa s, in each case measured at 25° C. and at a shear rate of $D=10\ s^{-1}$, e.g. measured with a Brookfield® viscometer according to DIN 53018.

Toothpastes according to the invention with viscosity values in the range of approximately 10-100 Pa s are referred to as liquid toothpastes, more viscous toothpastes according to the invention with a paste-like consistency normally found in the market on the other hand have viscosity values in the range of 150 to approximately 380 Pa s, preferably in the range of 180 to 350 Pa s.

Chewing gum, on the other hand, predominantly comprises a highly viscous mass, the viscosity of which hardly drops even after chewing for a long time and which does not dissolve during the chewing process either.

Accordingly the viscosities of gum bases normally used (and which form the basis for chewing gum) are higher than the viscosities of toothpastes. Measurement of the viscosity of gum bases is only possible at high temperature; normally for such gum bases viscosity values of approximately 200 Pa s at 90° C. are indicated. Due to the different structure and the different further properties of chewing gums and toothpastes, flavoring agents are probably released from the toothpaste and from the chewing gum in crucially different ways. In chewing gum, the flavoring agents are retained by the chewy chewing gum mass to a much greater extent and released only slowly. Conversely, flavoring agents in a toothpaste are released really very early, that is to say immediately in their full strength, when cleaning the teeth and therefore are perceived comparatively as very much stronger. From the current perspective, therefore, it is understandable why, in chewing gum, through the addition of just small quantities of modifiers, effects can be achieved, while in toothpaste and other teeth cleaning compounds this is not the case.

Moreover, it is also necessary to take into account that chewing gum normally contains very much larger quantities of sweet tasting substances than teeth cleaning compounds. These sweet tasting substances alone are able to lessen the sharp-bitter taste of menthol.

Teeth cleaning compounds according to the invention offer a range of advantages due to the presence of WS-12 as a masking agent for menthol:

In a teeth cleaning compound according to the invention the proportion of menthol (as component a) of a flavoring agent composition (ii)) can be comparatively high, without the inherent bitterness of the menthol being noticed or perceived as troublesome. If a high quantity of menthol is used, the fresh and cool sensation when using the teeth cleaning compound according to the invention (preferably toothpaste) is particularly pronounced and in this way the perception of those unpleasant taste sensations which are caused by the normally present teeth cleaning agents is lowered (see general comments above).

Particularly relevant teeth cleaning compounds according to the invention therefore contain active substances which themselves cause unpleasant taste sensations, thus in particular triclosan, potassium or zinc citrate, tin chloride, tin dichloride, tin fluoride, amine fluoride or cetylpyridinium chloride. Teeth cleaning compounds according to the invention also preferably contain a considerable proportion of menthol, which is preferably sufficient to mask in full or in part the taste notes perceived as unpleasant of the active substances contained in the teeth cleaning compounds. Preferred teeth cleaning compounds according to the invention contain menthol in the range of 0.15-1.3 wt. % in relation to the overall weight of the preferred teeth cleaning compound according to the invention. Particularly preferred teeth cleaning compounds according to the invention contain 0.4-0.9 wt. % of menthol in relation to the overall weight of the particularly preferred teeth cleaning compound according to the invention.

Here the menthol used can be used as a constituent of a flavoring agent composition of natural origin—in particular a peppermint oil composition with a proportion of menthol may be involved. Instead of or in addition to such a flavoring agent composition of natural origin, however, pure (for example synthetic) menthol may be added. A person skilled in the art will refer in this regard to linear additions of menthol to a base mixture. It is self-evident that a teeth cleaning compound according to the invention can contain a comparatively high proportion of a natural flavoring agent composition containing menthol and/or (linearly added) menthol, because the bitterness of the menthol is masked by the quantity of WS-12 used.

In a teeth cleaning compound according to the invention no other flavoring agents with a possibly strong taste need be present which in normal teeth cleaning compounds serve to mask the bitterness of menthol. While their presence in teeth cleaning compounds according to the invention is not therefore excluded, neither is it preferred. In particular a teeth cleaning compound according to the invention can contain anethole (see discussion above), but the (primary) importance of the anethole will then preferably not be in masking the bitter taste of the menthol.

In the teeth cleaning compounds according to the invention, in particular in the absence of strong-tasting flavoring agents the presence of other flavors with particularly palatable taste notes can be envisaged. In particular, advantageous teeth cleaning compounds according to the invention are those in which taste notes in the direction of fruit, cinnamon, wintergreen, eucalyptus, spearmint and peppermint are present. The quantity of flavoring used in each case, and which is responsible for the stated taste notes, can be low here, because, due to the presence of WS-12 as a bitterness masker for menthol, the to presence of, for example, anethole (as a bitterness masker with its own undesired properties) can be dispensed with. In individual cases, due to the presence of the abovementioned or other palatable taste notes, which are predominantly rated by the consumer as very pleasant, an unpleasant taste sensation originating from the primary active substances used can be further reduced.

Apart from the advantages discussed above of a teeth cleaning compound, there is a further advantage that is of particular commercial relevance. Teeth cleaning compounds according to the invention namely impart a particularly long and, compared with teeth cleaning compounds of the prior art, significantly extended cooling sensation of freshness, which arises for example after teeth-cleaning with a toothpaste according to the invention. This long-lasting, cooling sensation of freshness is dependent upon the presence of WS-12 in the teeth cleaning compound according to the invention.

Unlike teeth cleaning preparations according to the invention containing WS-12, teeth cleaning compounds with convention cooling agents, as described for example by M. Erman in Perfumer & Flavorist 32(10), 20-35 (2007) or M. L. Dewis in D. J. Rowe, Chemistry and Technology of Flavors and Fragrances, Blackwell Publishing Ltd, Oxford 2005, p. 212-222, lead only to a comparatively much shorter perception of a sensation of freshness. While comparable teeth cleaning compounds, containing said conventional active substances, do impart a cooling effect, which may even start relatively quickly after approximately 30 seconds, this tails off again relatively quickly after a high point at between three and five minutes, with the cooling being clearly perceptible for a total of a maximum of 30 minutes. In our own investigations in this regard the above-mentioned menthyl-3-carboxylic acid-N-ethyl amide proved to be a cooling agent which imparts a cooling effect only for a relatively short time. Our own comparative investigations have shown, moreover, that increasing the quantity of conventional cooling agents used does not prolong the sensation of freshness generated by the feeling of cold.

According to our own research, to date only one type of compound (2-isopropyl-5-methyl-cyclohexane carboxylic acid-(4-cyanomethyl-phenyl)-amide (CAS 852379-28-3)) is known, which because of its longer lasting cooling effect differs significantly from conventional cooling agents (cf. in this respect S. M. Furrer et al, Chem. Percept 1 (2008), 119-126). It is difficult for a person skilled in the art to find substances with an exceptionally long-lasting cooling effect, since the activity determined in-vitro through receptor bonding correlates with the intensity but not with the duration of the sensation of coolness (loc. cit, page 120).

It is particularly surprising that a teeth cleaning compound according to the invention consistently brings about a significantly extended sensation of freshness, which in most cases lasts at least twice as long as a sensation of freshness that is brought about by comparative teeth cleaning compounds containing one of the above-mentioned conventional cooling substances.

Particularly surprising is that with WS-12 (menthane carboxylic acid-N-(4-methoxyphenyl)-amide) a pleasant cooling effect coupled with a particularly long-lasting sensation of freshness can be achieved. Due to its high melting point of 177° C. the compound was predicted to have insufficient solubility in oral care flavors and thus inadequate bioavailability (loc cit., pages 121, 122).

With teeth cleaning compounds according to the invention, therefore, there are two further aspects which are of decisive importance for the present invention:

Firstly, the quantity of WS-12 used masks the bitter taste impressions of the menthol. Secondly, because of the presence of WS-12, along with menthol (and with the further component c)), the teeth cleaning compound imparts a particularly long-lasting sensation of freshness.

In a teeth cleaning compound according to the invention, the task of component c) of the flavoring agent composition is to solubilize the quantity of WS-12 in the teeth cleaning compound necessary for masking bitterness, thereby making it available for the purposes of masking bitterness. It transpires that in comparable teeth cleaning compounds containing no component c), the dissolved quantity of WS-12 is generally too low to be able to bring about effective masking of the menthol used. According to the invention, an optional substance with a log-$K_{ow}$ value in the range of 1.5-5 is not or not exclusively used in order to achieve the necessary solubility of WS-12 in the composition as a whole, but rather at least one, two or more flavoring agents are used which have a corresponding log-$K_{ow}$ value. In a teeth cleaning compound according to the invention, the presence of substances with a log-$K_{ow}$ value in the range of 1.5-5 and which are not at the same time a flavoring agent is preferably dispensed with. Instead of such non-flavoring agent substances, the use of corresponding flavoring agents is namely to preferred.

The log-$K_{ow}$ value is a measure of the polarity of a substance. The log-$K_{ow}$ designates the log 10 of the distribution coefficient of a substance between 1-octanol (nonpolar) and water (polar).

In practice the log-$K_{ow}$ value is determined by calculation, with the molecular structure of the substance whose log-$K_{ow}$ value is to be determined being used as a basis. In the context of the present text, the term "log-$K_{ow}$ value" designates the value calculated on the basis of the respective molecular structure using the "EPIWIN" software program by P. Howard and W. Meylan [Version 2.2]. This software program can be obtained from Syracuse Research Corporation, Merrill Lane, Syracuse, N.Y. 13210, USA.

Preference is for a teeth cleaning compound according to the invention wherein the, a plurality or all further flavoring agents are selected with a log-$K_{ow}$ value in the range of 1.5-5 from the group consisting of menthone, isomenthone, carvone, 1,2-dihydrocarvone, anethole, piperitone, menthyl acetate, menthyl methyl ether, 1,8-cineole, cinnamaldehyde and methyl salicylate, preferably from the group consisting of menthone, isomenthone, carvone and piperitone.

As component c) of a flavoring agent composition (ii) of a teeth cleaning compound according to the invention a single or two or more flavoring agents from said group in combination with each other can therefore also be used.

Preferred flavoring agents that can be used as a component or in component c) of the teeth cleaning compound according to the invention are indicated in the following with the log-$K_{ow}$ values calculated using the EPWIN program in brackets: menthone (2.87), isomenthone (2.87), carvone (3.07), 1,2-dihydrocarvone (2.86), anethole (3.39), piperitone (3.07), menthyl acetate (4.39), 1,8-cineole (3.13), cinnamaldehyde (1.82) and methyl salicylate (2.60).

Preferred enantiomers of the particularly preferred flavoring agents of constituent (c) are (−)-menthone (2.87), (+)-isomenthone (2.87), (−)-carvone (3.07) and (−) piperitone (3.07).

Preference is for the use of flavoring agents from the abovementioned group in or as component c) of a teeth cleaning compound according to the invention, wherein the log-$K_{ow}$ value of the respective flavoring agent is in the range of 1.8-4.5.

Quite particular preference is for a teeth cleaning compound according to the invention as to defined above, wherein the or at least one of the further flavoring agents is menthone.

Surprisingly here it transpires that said flavoring agents of component c) in the teeth cleaning compound according to the invention for their part can have a bitter taste without this being a disadvantage. Thus, for example, the particularly preferred flavoring agents menthone and isomenthone, described in "Perfume and Flavor Chemicals" by Steffen Arctander (published 1969) under the substance numbers 1843 (menthone) and 1844 (isomenthone) have a bitter taste.

In such teeth cleaning compounds, which apart from the bitter tasting substance menthol contain one, two or more bitter tasting flavoring agents as component c)), the quantity of WS-12 used masks not only the bitterness of the menthol but also (in part at least) the bitterness of said further flavoring agent(s). A person skilled in the art will need little advance testing to determine which quantities of WS-12 (as component b)) and of the one, two or more flavoring agents he needs to use in order not to exceed a certain maximum bitterness. In doing so he will in particular take into account whether a further flavoring agent to be used itself imparts a bitter taste impression or is merely used in order to provide sufficient solubility of WS-12 in the teeth cleaning compound according to the invention.

If a teeth cleaning compound according to the invention contains, in addition to menthol, one or more bitter-tasting substances, the effects of which in terms of bitterness are indistinguishable, then the quantity of WS-12 used is referred to as the "the quantity masking the bitterness of the menthol", if the overall bitterness of the teeth cleaning compound is reduced because of the presence of WS-12.

The one, two or more flavoring agents with a log-$K_{ow}$ value in the range of 1.5-5 are preferably aprotic flavoring agents.

The flavoring agents of the component c) of a teeth cleaning compound according to the invention can be used in the form of an essential oil containing this substance. Particular preference is for the combined use of pure flavoring agents together with flavoring agents in which one or more essential oils are present. The flavoring agents combined in this way then form, together, the component c) of a teeth cleaning compound according to the invention.

A teeth cleaning compound according to the invention is not a chewing gum; it therefore contains at most 0-10 wt. % of a chewing gum base in relation to the overall weight of the teeth cleaning compound, preferably 0-3 wt. % of a chewing gum base, particularly preferably no chewing gum base (0 wt. %). At the same time or alternatively, a preferred teeth cleaning compound according to the invention contains at most one or more elastomers in an overall quantity of 0-20 wt. %, in relation to the overall weight of the teeth cleaning compound (cf. in this respect Example 11 below, in which Poloxamer 407 and polyethylene glycol are regarded as elastomers).

Our own investigations have shown that in particular in the presence of WS-12 in combination with further flavoring agents, as are used for aromatizing in conventional oral hygiene applications, a fundamentally different cold profile is imparted from the cooling substances of the prior art. Depending on the exact composition, when cleaning the teeth with a toothpaste according to the invention and containing a flavor with WS-12, a sensation of cold is perceptible for up to 2 hours.

The particularly long-lasting cold sensation is achieved in particular by teeth cleaning compounds according to the invention in which WS-12 is combined with 1,8-cineole (eucalyptol), menthone, carvone, cinnamaldehyde and/or methyl salicylate. It is a case here of flavoring agents, which have already been discussed above as a constituent of the component c). Said flavoring agents thus perform two tasks in a preferred teeth cleaning compound according to the invention: firstly they increase the solubility of WS-12 to the extent that a quantity of WS-12 can be used that is sufficient to mask the bitterness of the menthol. Secondly, they prolong the cooling effect of the teeth cleaning compound according to the invention even more.

It is self-evident that said flavoring agents can be used in the form of flavoring mixtures. Preference is therefore for a teeth cleaning compound according to the invention containing
  eucalyptus flavors containing eucalyptol;
  peppermint flavors containing menthone;
  spearmint flavors containing carvone;
  cinnamon flavors containing cinnamaldehyde;
  wintergreen flavors containing methyl salicylate.

A teeth cleaning compound according to the invention as defined above (in particular as designated above as preferred) preferably also contains further constituents or components. Preference is for such a teeth cleaning compound according to the invention to
  also contain sugar substitutes, preferably non-cariogenic sugar substitutes,
and/or
  be free of saccharose, glucose and fructose, preferably completely free of cariogenic sugars,
and/or
  also contain humectants, preferably a humectant sugar alcohol, preferably sorbitol or xylitol,
and/or
  also contain thickening agents,
and/or
  also contain one or more surfactants, preferably sodium lauryl sulfate,
and/or
  also contain one or more antimicrobial agents, preferably selected from the group consisting of hydroxybenzoic acid esters, parabens, triclosan
and/or
  also contain one or more colorings
and/or
  also contain one or more anticaries agent, preferably contain one or more fluorides
and/or
  also contain one or more further physiological cooling agents.

Particular preference for use in teeth cleaning compounds according to the invention is for sugar substitutes involving sweetening agents such as artificial sweeteners and sugar substitutes or mixtures thereof selected from the group consisting of:
  artificial sweeteners such as in particular acesulfame-K, aspartame, cyclamate (and the Na- and Ca-salts thereof), neohesperidin dihydrochalcone, sucralose and saccharin (and the Na-, K- and Ca-salts thereof). Sweeteners of vegetable origin can likewise be used such as for example glycyrrhizin and thaumatin. Particular preference is for acesulfame-K, aspartame, cyclamate, Na-cyclamate, saccharin, Na-saccharin and sucralose;

and sugar substitutes, preferably sugar alcohols, in particular isomaltitol (E 953), lactitol (E 966), maltitol, mannitol (E 421), sorbitol (E 420), xylitol (E 967) and mixtures thereof.

In combinations of WS-12 (as component b) of a teeth cleaning compound according to the invention) with diols (as additional sugar substitute in a teeth cleaning compound according to the invention), in particular in combination with 1,2-(alkane-)diols, here preferably 1,2-propylene glycol, 1,2-pentanediol, 1,2-octanediol), triols, here in particular glycerin, or polyols, here preferably sugar alcohols, such as isomaltitol (E 953), lactitol (E 966), maltitol, mannitol (E 421), sorbitol (E 420), xylitol (E 967) and mixtures thereof sugar alcohols, it was also surprisingly found that the cooling effect of WS-12 is significantly prolonged. The preferred overall quantity of diols, triols and polyols in a teeth cleaning compound according to the invention is preferably in the range of 0.5-50 wt. %, preferably in the range of 2-45 wt. %, most preferably in the range of 5-40 wt. %, in each case in relation to the overall weight of the teeth cleaning compound according to the invention.

A preferred teeth cleaning compound is free from saccharose, glucose and fructose and preferably completely free from cariogenic sugars. This is naturally the case in particular if a preferred teeth cleaning compound according to the invention contains sugar substitutes, preferably non-cariogenic sugar substitutes as discussed above. A person skilled in the art will decide on a case by case basis if cariogenic sugars are to or can be dispensed with completely in a teeth cleaning compound according to the invention, and he will provide corresponding quantities of sugar substitutes in order to meet the needs of consumers.

A preferred teeth cleaning compound according to the invention (in particular a teeth cleaning compound according to the invention already designated as preferred above) also contains humectants (e.g. glycerin). Such humectants are preferably sugar alcohols such as for example sorbitol or xylitol. Thus the use of a humectant sugar alcohol simultaneously corresponds to the use of a sugar substitute and a humectant.

A preferred teeth cleaning compound according to the invention (in particular a teeth cleaning compound according to the invention already designated as preferred above) also contains thickening agents, preferably selected from the group consisting of: polyethylene glycols, Laponite®, carboxymethylcellulose, xanthan, tragacanth, carob gum, to gellan, guar gum, gum Arabic, carrageenans, alginic acid, alginates, pectines, pyrogenic silicic acid, bentonites, magnesium-aluminum-silicates and mixtures thereof. Particularly suitable as thickening agents for use in a teeth cleaning compound according to the invention are the hydrocolloids among those mentioned.

A preferred teeth cleaning compound according to the invention (in particular a teeth cleaning compound already designated as preferred above) also contains one or more surfactants, preferably sodium lauryl sulfate, sodium lauryl sarcosinate and/or cocamidopropyl betaine, with particular preference for sodium lauryl sulfate. Generally, in a teeth cleaning compound according to the invention, anionic, zwitterionic, amphoteric, non-ionic tensides or a combination of a plurality of these tensides can be used.

A teeth cleaning compound according to the invention (in particular a teeth cleaning compound according to the invention already designated as preferred above) preferably also contains one or more antimicrobial agents, which are preferably selected from the group consisting of hydroxybenzoic acid esters, parabens and triclosan. The antimicrobial agents can for example act as a preservative or antiplaque agent. p-hydroxybenzoic acid methyl-, ethyl or propyl esters can in particular be used as hydroxybenzoic acid esters. Instead of the antimicrobial agents already mentioned above, or in addition to these, in some cases sodium sorbate, sodium benzoate, bromochlorophene, phenyl-salycic acid esters, biguanides (e.g. chlorohexidine) and/or thymol are preferably used.

In some cases preference is also for the use as antimicrobial agents of bactericides such as phenols, resorcins, bisphenols, salicylanilides and their halogenated derivatives, halogenated carbanilides and p-hydroxybenzoic acid esters. Triclosan, the use of which is particularly preferred, is a halogenated diphenyl ether, namely 2,4,4'-trichloro-2'-hydroxy diphenyl ether. Instead of or in addition to triclosan, other halogenated diphenyl ethers can be used, e.g. 2,4-dichloro-2'-hydroxy diphenyl ether, 4,4'-dichloro-2'-hydroxy diphenyl ether or 2,4,4'-tribromo-2'-hydroxy diphenyl ether. Halogenated diphenyl ethers such as for example triclosan are preferably used in an overall quantity of 0.01-1 wt. % in a teeth cleaning compound according to the invention. Triclosan itself is particularly preferred in a quantity of 0.01 to 0.3 wt. %.

A teeth cleaning compound according to the invention (in particular a teeth cleaning compound according to the invention already designated as preferred above) preferably also contains one or more colorings. These colorings are preferably present in a quantity that is sufficient to provide the corresponding teeth cleaning compound with a desired color. The quantity used of typical colorings is therefore approximately 2-5 wt. %, in relation to the overall weight of the teeth cleaning compound according to the invention. A proportion of approximately 3 wt. % of colorings is often suitable. The colorings used can be natural food colorings and colorings that are suitable for food, drug and cosmetic applications. Suitable colorings are known as FD & C colorings and dyes. The colorings to be used are preferably soluble in water. Examples of suitable colorings include indigo dye which is known as FD & C Blue No. 1 and FD & C Yellow No. 10. A complete list of FD & C dyes and their corresponding structures can be found in Kirk-Othmer, Encyclopedia of Chemical Technology, $3^{rd}$ Edition, Volume 5, pages 857-884.

Dyes to be used can also perform the function of an opacifier. Thus, for example, titanium dioxide can be incorporated in quantities of up to preferably 3 wt. %, preferably 1 wt. %, and quite particularly preferably 0.5 wt. % in a teeth cleaning compound according to the invention, in relation to the overall weight of the teeth cleaning compound according to the invention.

A teeth cleaning compound according to the invention (in particular a teeth cleaning compound according to the invention already designated as preferred above) preferably also contains one or more anticaries agents. The anticaries agent or agents is or are usually one or more fluorides, wherein organic or inorganic fluorides may be used. Preferred fluorides for use in a teeth cleaning compound according to the invention are for example sodium fluoride, potassium fluoride, sodium monofluorophosphate, quaternary ammonium fluoride and sodium fluorosilicate. Zinc fluoride and tin-(II)-fluoride are also used by preference in individual cases. Preference is for the use of an overall quantity of 0.01-0.2 wt. % of fluoride in the form of one of the stated fluorides or in the form of another compound that makes fluoride available in a suitable manner.

A teeth cleaning compound according to the invention (in particular a teeth cleaning compound according to the invention already designated as preferred above) preferably also contains one or more further physiological cooling agents. Here the further cooling agent(s) are preferably selected from the group consisting of: menthyl ethers (for example (l-menthoxy)-1,2-propanediol, (l-menthoxy)-2-methyl-1,2-propanediol, 1-menthyl-methyl ether), menthyl esters (for example menthyl formiate, menthyl acetate, menthyl isobutyrate, menthyl lactate, preferably L-menthyl lactate, L-menthyl-L-lactate, L-menthyl-D-lactate, menthyl-(2-methoxy)acetate, menthyl-(2-methoxyethoxy)acetate, menthyl pyroglutamate), menthyl carbonates (for example menthyl alkyl carbonates, menthyl propylene glycol carbonate, menthyl ethylene glycol carbonate, menthyl glycerin carbonate or mixtures of these), the half-esters of menthols with a dicarboxylic acid or derivatives thereof (for example mono-menthyl succinate, mono-menthyl glutarate, mono-menthyl malonate, O-menthyl succinic acid ester-N,N-(dimethyl)amide, O-menthyl succinic acid ester amide), menthane carboxylic acid amides (for example menthane carboxylic acid-N-ethyl amide [WS-3], $N^\alpha$-(menthane carbonyl) glycine ethyl ester [WS-5], menthane carboxylic acid-N-(4-cyanophenyl)amide, menthane carboxylic acid-N-(alkoxyalkyl)amides), menthone and menthone derivatives (for example menthone ketals such as L-menthone glycerin ketal), 2,3-dimethyl-2-(2-propyl)-butyric acid derivatives (for example 2,3-dimethyl-2-(2-propyl)-butyric acid-N-methyl amide [WS-23]), isopulegol or its esters (l-(−)-isopulegol, l-(−)-isopulegol acetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopenten-1-one) or tetrahydropyrimidin-2-one (for example icilin or related compounds, as described in WO 2004/026840), N-(4-cyanomethylphenyl)-p-menthane carboxamide, N-(2-(pyridin-2-yl)ethyl)-3-p-menthane carboxamide, acetic acid-2-(methylamino)-2-oxo-, 5-methyl-2-(1-methylethyl)cyclohexyl esters, acetic acid-2-(ethylamino)-2-oxo-, 5-methyl-2-(1-methylethyl)cyclohexyl esters. Cooling agents with a menthol structure as their base are generally preferred derivatives of L-menthol.

Preference is for the use of one or more physiological cooling agents, which while bringing about a physiological cooling effect, at the same time do not have any or any significant effect on taste. Preferred physiological cooling agents are therefore selected from the group consisting of: menthyl ethers (for example (l-menthoxy)-1,2-propanediol, (l-menthoxy)-2-methyl-1,2-propanediol), polar menthyl esters (for example menthyl lactates, L-menthyl-L-lactate, L-menthyl-D-lactate, menthyl-(2-methoxy)acetate, menthyl-(2-methoxyethoxy)acetate, menthyl pyroglutamate), menthyl carbonates (for example menthyl propylene glycol carbonate, menthyl ethylene glycol carbonate, menthyl glycerin carbonate), the half-esters of menthols with a dicarboxylic acid or derivatives thereof (for example mono-menthyl succinate, mono-menthyl glutarate, mono-menthyl malonate, O-menthyl succinic acid ester-N,N-(dimethyl) amide, O-menthyl succinic acid ester amide), menthane carboxylic acid amides not according to the invention (for example menthane carboxylic acid-N-ethyl amide [WS-3], $N^\alpha$-(menthane carbonyl)glycine ethyl ester [WS-5], menthane carboxylic acid-N-(4-cyanophenyl)amide, menthane carboxylic acid-N-(alkoxyalkyl)amides), menthone derivatives (for example L-menthone glycerin ketal), 2,3-dimethyl-2-(2-propyl)-butyric acid derivatives (for example 2,3-dimethyl-2-(2-propyl)-butyric acid-N-methyl amide), pyrrolidone derivatives of cycloalkyldione derivatives (for example 3-methyl-2(1-pyrrolidinyl)-2-cyclopenten-1-one), 2,2,2-trialkyl acetic acid amides (for example 2,2-diisopropyl propionic acid methyl amides) or tetrahydropyrimidin-2-ones (for example icilin, icilin-derivatives or related compounds as described in WO 2004/026840).

The overall quantity of further physiological cooling agents which, in addition to WS-12 are present by way of additional constituent in a teeth cleaning compound according to the invention, is preferably in the range of 0.01-3.0 wt. %, preferably in the range of 0.025-1.0 wt. %, more preferably in the range of 0.05-0.50 wt. %, in each case in relation to the overall weight of teeth cleaning compound according to the invention.

A teeth cleaning compound according to the invention contains as component c) one, two or more further flavoring agents. Here not all, but at least one, of these further flavoring agents have a log-$K_{ow}$ value in the range of 1.5-5. In some cases it is advantageous to provide for a flavoring agent mixture as component c) of the flavoring agent composition to be used according to the invention, in which not all the further flavoring agents have a log-$K_{ow}$ value in the range of 1.5-5.

Suitable flavoring agents (with a log-$K_{ow}$ value in the range of 1.5-5 or with a log-$K_{ow}$ value outside of this range) are natural raw materials such as vegetable extracts and essential oils, or fractions obtained and substances isolated from these, as well as individual flavoring agents obtained synthetically or through biotechnological means.

Preferred natural raw materials are selected from the group consisting of: peppermint oils, spearmint oils, *Mentha arvensis* oils, aniseed oils, clove oils, citrus oils, cinnamon bark oils, wintergreen oils, cassia oils, davana oils, spruce needle oils, eucalyptus oils, fennel oils, galbanum oils, ginger oils, chamomile oils, caraway oils, rose oils, geranium oils, sage oils, yarrow oils, star anise oils, thyme oils, juniper berry oils, rosemary oils, Angelica root oils, and fractions of these oils.

Preferred individual compounds, which can be used by way of further flavoring agent in component c) of a teeth cleaning compound according to the invention, are selected from the group consisting of: anethole, menthone, isomenthone, menthyl acetate, to menthofuran, menthyl methyl ether, mint lactone, eucalyptol, limonene, eugenol, pinene, sabinene hydrate, 3-octanol, carvone, gamma-octalactone, gamma-nonalactone, germacrene D, viridiflorol, 1,3E,5Z-undecatriene, isopulegol, piperitone, 2-butanone, ethyl formiate, 3-octyl acetate, isoamyl isovalerianate, hexanol, hexanal, cis-3-hexenol, linalool, alpha-terpineol, cis and trans carvyl acetate, p-cymol, thymol, 4,8-dimethyl-3,7-nonadien-2-one, damascenone, damascone, rose oxide, dimethyl sulfide, fenchol, acetaldehyde diethylacetal, cis-4-heptenal, isobutyraldehyde, isovaleraldehyde, cis-jasmone, anisaldehyde, methyl salicylate, myrtenyl acetate, 8-ocimenyl acetate, 2-phenyl ethyl alcohol, 2-phenyl ethyl isobutyrate, 2-phenyl ethyl isovalerate, cinnamaldehyde, geraniol, nerol. In chiral compounds the said flavoring agents can be present in the form of racemate, an individual enantiomer or enantiomer-enriched mixtures. Regarding the disadvantages that arise with the use of larger quantities of anethole, refer to our statements above. A person skilled in the art will take into account the advantages and disadvantages of the individual flavoring agents or the individual natural raw materials and the ability of the respective overall flavoring agent compositions to mask unpleasant taste impressions when formulating a teeth cleaning compound according to the invention.

In many cases teeth cleaning compounds according to the invention are preferred which in component c) contain further flavoring agents which bring about a spicy taste or a sensation of hotness or heat on the skin and mucous membranes or a prickling or tingling sensation in the mouth and oral cavity, such as for example paprika powder, chilli pepper powder, paprika extracts, pepper extracts, chilli pepper extracts, ginger root extracts, extracts from grains of paradise (*Aframomum melegueta*), paracress extracts (*Jambu oleoresin; Spilanthes acmella*, or *Spilanthes oleracea*), Japanese pepper extracts (*Zanthoxylum piperitum*), *Kaempferia galanga* extracts, *Alpinia galanga* extracts, water pepper extracts (*Polygonium hydropiper*), capsaicin, dihydrocapsaicin, gingerol, paradol, shogaol, piperine, sanshool I, sanshool II, sanshoamide, spilanthol, carboxylic acid-N-vanillylamides, in particular nonanbic acid-N-vanillylamide, 2-nonenoic acid amides, in particular 2-nonenodic acid-N-isobutylamide, 2-nonenoic acid-N-4-hydroxy-3-methoxyphenylamide, alkyl ethers of 4-hydroxy-3-methoxybenzyl alcohol, in particular 4-hydroxy-3-methoxybenzyl n-butyl ether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylenedioxybenzyl alcohol, acetals of vanillin, acetals of ethyl vanillin, acetals of isovanillin, (4-hydroxy-3-methoxyphenyl)acetamides, in particular (4-hydroxy-3-methoxyphenyl)acetic acid-N-n-octylamide, allyl isothiocyanate, nicotinaldehyde, methyl nicotinate, propyl nicotinate, 2-butoxyethyl nicotinate, benzyl nicotinate, 1-acetoxychavicol.

In many cases preference is for teeth cleaning compounds according to the invention, which in component c) contain one, two or more further flavoring agents with no physiological cooling action. In addition to their actual odorous aroma value, such flavoring agents also cause a taste impression, a taste-modulating effect or a trigeminal or salivatory stimulus, but not a cooling stimulus. The flavoring agents used preferably bring about a taste impression selected from the group consisting of sweet, umami, bitter, salty and sour. Preferred taste-modulating effects are selected from the group consisting of bitter-masking, umami-enhancing, sweet-enhancing, salt-enhancing and sour-masking effects. Preferred trigeminal stimuli brought about by such flavoring agents are selected from the group consisting of spiciness, heat, tingling and pungency.

Preference is for the use of taste-modulating flavoring agents (including flavoring agents) wherein these are preferably selected from the group consisting of adenosine 5'-monophosphate, cytidine 5'-monophosphate, guanosine monophosphate, inosine 5'-monophosphate, inositol phosphate, and the pharmaceutically acceptable salts thereof; lactisoles; 2,4-dihydroxybenzoic acid; 3-hydroxybenzoic acid; sodium salts, preferably sodium chloride, sodium lactate, sodium citrate, sodium acetate, sodium gluconate, sodium glutamate; 2-phenoxy propionic acid; hydroxyflavanones, such as for example eriodictyol, homoeriodictyol, and the sodium salts and hydroxyflavanones thereof in accordance with US 2002/0188019; hydroxybenzoic acid amides, such as for example 2,4-dihydroxybenzoic acid vanillylamide, 2,4-dihydroxybenzoic acid-N-(4-hydroxy-3-methoxybenzyl)amide, 2,4,6-tri hydroxybenzoic acid-N-(4-hydroxy-3-methoxybenzyl)amide, 2-hydroxybenzoic acid-N-(4-hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl)amide monosodium salt, 2,4-dihydroxybenzoic acid-N-2-(4-hydroxy-3-methoxyphenyl)ethyl amide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl) ethyl]amide; 4-hydroxybenzoic acid vanillylamide (in particular as described in WO 2006/024587, which is incorporated into this application by way of reference with regard to the corresponding compounds disclosed therein); hydroxydeoxybenzoins, such as for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl) ethanone, 1-(2-hydroxy-4-methoxyphenyl)-2-(4-hydroxy-3-methoxyphenyl)ethanone) (in particular those as described in WO 2006/106023, which is incorporated into this application by way of reference with regard to the corresponding compounds disclosed therein); hydroxyphenylalkadiones, such as for example gingerdione-[2], gingerdione-[3], gingerdione-[4], dehydrogingerdione-[2], dehydrogingerdione-[3], dehydrogingerdione-[4]) (in particular those as described in WO 2007/003527, which is incorporated into this application by way of reference with regard to the corresponding compounds disclosed therein); diacetyl trimers (in particular those as described in WO 2006/058893, which is incorporated into this application by way of reference with regard to the corresponding compounds disclosed therein); γ-aminobutyric acid as described in WO 2005/096841, which is incorporated into this application by way of reference with regard to the corresponding compounds disclosed therein), divanillin as described in WO 2004/078302 and hesperetin according to WO 2007/014879.

Preference is also for the use of flavoring agents without a physiological cooling action and so in particular of salivatory substances such as pellitorine according to WO 04/000787 or US 2004/0241312 and alkamides according to DE 103 51 422.

A teeth cleaning compound according to the invention contains as component (i) cleaning granules. Here the term cleaning granules includes in particular the normal abrasive systems found in teeth cleaning compounds, such as grinding or polishing agents. The cleaning granules to be used according to the invention are suitable for carefully removing plaque from the tooth enamel, that is to say with low abrasion of the enamel or dentine. The cleaning granules to be used according to the invention as component (i) are preferably selected from the group consisting of (preferably precipitated) silicic acids, calcium carbonate, calcium phosphates, aluminum oxides, hydroxylapatites, organic cleaning granules (such as polymethacrylate-based cleaning granules) and mixtures of these.

A person skilled in the art will be aware that some of the abovementioned further constituents of a preferred teeth cleaning compound according to the invention themselves impart unpleasant and in many cases above all bitter or metallic taste impressions. Surprisingly, however, in connection with the present invention it transpires that the overall flavoring agent composition comprising a) menthol, b) a quantity of WS-12 to mask the bitterness of the menthol and c) the further flavoring agents with log-$K_{ow}$ values of 1.5-5 is suitable for masking these unpleasant (in particular bitter or metallic) taste impressions as well. The quantity of WS-12 used is probably responsible for this. To the extent that the quantity of WS-12 used masks the overall bitterness of the teeth to cleaning compound, for the purposes and from an understanding of the present text, a quantity of WS-12 to mask the bitterness of the menthol is present. In particular the flavoring agent composition to be used according to the invention with the components a), b) and c) masks unpleasant, above all bitter or metallic, taste impressions, such as those caused by substances such as triclosan, zinc citrate, zinc sulfate, poly- and pyrophosphates, bicarbonates (e.g. sodium bicarbonate), strontium- and potassium salts (for example potassium citrate, potassium nitrate, potassium chloride, strontium chloride), tin pyrophosphate, tin chloride, aluminum lactate, hydrogen peroxide, fluorides, vitamins, cetylpyridinium chloride and by emulsifiers, such as for example sodium lauryl sulfate, sodium lauryl sarcosinate and cocamidopropyl betaine as well as by sweeteners such as aspartame, saccharin, acesulfame-K, sorbitol, xylitol, cyclamates (for example sodium cyclamate), sucralose, alitame, neotame, thaumatin, neohesperidin dihydrochalcone, maltitol, lactitol or also brought about by certain chewing gum masses (gum bases) and mixtures thereof.

In teeth cleaning compounds according to the invention, the weight ratio of WS-12 to menthol can vary widely, depending on the (masking) outcome sought. In many cases, however, teeth cleaning compounds according to the invention (in particular teeth cleaning compounds according to the invention already designated as preferred above), are preferred in which the weight ratio of menthane carboxylic acid-N-(4-methoxyphenyl)-amide (WS-12) to menthol is 1:5-1:1000, preferably in the range of 1:10-1:500, preferably in the range of 1:10-1:250, quite preferably in the range of 1:10-1:150.

The abovementioned preferred weight ratios of WS-12 to menthol apply in particular for toothpaste compounds according to the invention and in fact in particular for those toothpaste compounds according to the invention which contain peppermint oils.

In teeth cleaning compounds according to the invention, the weight ratio of WS-12 to the overall quantity of further flavoring agents (component c) of the flavoring agent composition (ii) to be used according to the invention) can vary widely. However, certain weight ratios of WS-12 to the overall quantity of the further flavoring agents are preferred, in particular those where the weight ratio of WS-12 to menthol is also within the preferred ranges discussed above. Particular preference is for teeth cleaning compounds according to the invention, in particular teeth cleaning compounds, in which the weight ratio of WS-12 to menthol has already been set at a value of 1:5-1:1000, in which the weight ratio of WS-12 to the overall quantity of further flavoring agents with a log-$K_{ow}$ value in the range of 1.5-5 is a maximum of 1:10, preferably a maximum of 1:20 and particularly preferably a maximum of 1:40, wherein this weight ratio is preferably in the range of 1:10-1:200, preferably in the range of 1:20-1:150, particularly preferably in the range of 1:40-1:100.

With regard to the weight ratio of WS-12 to menthol, tiered preferred ranges are indicated above. Similarly for the weight ratio of WS-12 to the overall quantity of further flavoring agents with a log-$K_{ow}$ value in the range of 1.5-5, tiered preferred ranges are given. Where both weight ratios discussed are in the respective preferred ranges, it is further preferred if at least one of the weight ratios is in a particularly preferred range, but quite particular preference is for combinations in which both the weight ratio of WS-12 to menthol and also the weight ratio of WS-12 to the further flavoring agents with a log-$K_{ow}$ value in the range of 1.5-5 are in particularly preferred ranges.

With regard to the weight ratio of WS-12 to the overall quantity of the further flavoring agents with a log-$K_{ow}$ value in the range of 1.5-5, it is pointed out that in order to achieve a long-lasting sensation of cold in a large number of cases the weight ratio of WS-12 to the overall quantity of the further flavoring agents with a log-$K_{ow}$ value in the range of 1.5-5 should be a maximum of 1:10. It is thus preferred if said flavoring agents make up at least ten times the quantity by weight of the quantity of WS-12 used. Preference is for at least twenty times the quantity by weight and particular preference for at least forty times the quantity by weight of said flavoring agents with a log-$K_{ow}$ value in the range of 1.5-5.

Preference is for teeth cleaning compounds according to the invention, in which the overall proportion of menthane carboxylic acid-N-(4-methoxyphenyl)-amide (WS-12) is in the range of 0.00015-0.26 wt. %, preferably in the range of 0.0003-0.13 wt. %, preferably in the range of 0.0006-0.13 wt. %, particularly preferably in the range of 0.001-0.13 wt. %, in particular preferably in the range of 0.0016-0.09 wt. %, quite particularly preferably in the range of 0.0027-0.09 wt. %, in relation to the overall weight of the teeth cleaning compound.

These preferred overall proportions of WS-12 are sufficient in a large number of cases to completely neutralize the bitterness of the menthol that is simultaneously present. Preferred overall quantities of menthol to be used in teeth cleaning compound according to the invention arise on the basis of the preferred overall proportions of menthol taking into account the preferred weight ratios of WS-12 to menthol, as discussed above. The result of this is a preferred overall proportion of menthol in a teeth cleaning compound according to the invention of 2 wt. % or less, preferably of 0.15-1.3 wt. %, particularly preferably of 0.4-0.9 wt. %.

In a teeth cleaning compound according to the invention with a particularly preferred proportion of menthol in the range of 0.4-0.9 wt. %, in relation to the overall weight of the teeth cleaning compound, the overall proportion of menthane carboxylic acid-N-(4-methoxyphenyl)-amide (WS-12) is preferably in the range of 0.0004-0.18 wt. %, more preferably in the range of 0.0008-0.09 wt. %, particularly preferably in the range of 0.0016-0.09 wt. %, and most preferably in the range of 0.0027-0.09 wt. %, in relation to the overall weight of the teeth cleaning compound.

Quite particular preference is for a teeth cleaning compound according to the invention comprising:
(i) cleaning granules
(ii) a flavoring agent composition comprising:
   a) menthol in a quantity of 0.15-1.3 wt. %, preferably in a quantity of 0.4-0.9 wt. %;
   b) a quantity of menthane carboxylic acid-N-(4-methoxyphenyl)-amide (WS-12) for masking the bitterness of the menthol in the range of 0.00015-0.26 wt. %, wherein the weight ratio of menthane carboxylic acid-N-(4-methoxyphenyl)-amide (WS-12) to menthol is in the range of 1:5-1:1000, and
   c) one, two or more further flavoring agents, wherein the, a plurality or all of the further flavoring agents have a log-$K_{ow}$ value in the range of 1.5-5 and wherein the weight ratio of menthane carboxylic acid-N-(4-methoxyphenyl)-amide (WS-12) to the overall quantity of the further flavoring agents with a log-$K_{ow}$ value in the range of 1.5-5 is a maximum of 1:10, wherein the wt. % details refer to the overall weight of the teeth cleaning compound.

The present invention also concerns the use of menthane carboxylic acid-N-(4-methoxyphenyl)-amide (WS-12) to mask the bitter taste of menthol in a teeth cleaning compound,
wherein the menthane carboxylic acid-N-(4-methoxyphenyl)-amide (WS-12) for the purposes of masking is present in or added to a mixture with
one, two or more further flavoring agents, wherein the, a plurality or all of the further flavoring agents have a log-$K_{ow}$ value in the range of 1.5-5.

It is self-evident that, concerning the use according to the invention, the preferred embodiments discussed above with a view to the teeth cleaning compound according to the invention apply accordingly.

Thus in particular a use according to the invention is preferred wherein the, a plurality or all of the further flavoring agents are selected from the group consisting of menthone, isomenthone, carvone, 1,2-dihydrocarvone, anethole, piperitone, menthyl acetate, menthyl methyl ether, 1,8-cineole, cinnamaldehyde and methyl salicylate, preferably from the group consisting of menthone, isomenthone, carvone and piperitone.

Similarly preferred is a use according to the invention (in particular the above use designated as preferred), wherein in the mixture the weight ratio of menthane carboxylic acid-N-(4-methoxyphenyl)-amide (WS-12) to the overall quantity of the further flavoring agents with a log-$K_{ow}$ value in the range of 1.5-5 is 1:10-1:200, preferably in the range of 1:20-1:150, particularly preferably in the range of 1:40-1:100.

The present invention also concerns a method for the dissolution of menthane carboxylic acid-N-(4-methoxyphenyl)-amide (WS-12) in a teeth cleaning compound containing menthol, wherein
menthol, preferably 5-1000 parts by weight of menthol, preferably 10-500 parts by weight of menthol, particularly preferably 10-250 parts by weight, quite particularly preferably 10-150 parts by weight of menthol,
1 part by weight of menthane carboxylic acid-N-(4-methoxyphenyl)-amide (WS-12) and
a total of 10-200, preferably 20-150, particularly preferably 40-100 parts by weight of one, two or more further flavoring agents, wherein the, a plurality or all of the further flavoring agents have a log-$K_{ow}$ value in the range of 1.5-5,
and
further teeth cleaning components are mixed together.

This aspect of the invention can be traced back to the surprising finding that the WS-12 used in connection with the present invention as a masking agent in a teeth cleaning compound containing menthol can only be solubilized in sufficient quantities if substances with a log-$K_{ow}$ value in the range of 1.5-5 are present. According to the invention these substances with a log-$K_{ow}$ value in the range of 1.5-5 are further flavoring agents, so that, apart from the aspect that is crucial for the solubility, further positive properties of a resulting teeth cleaning compound concerning the taste impressions imparted also arise.

The present invention also concerns a method for masking the bitterness of menthol in a teeth cleaning compound with the following step:
mixing of
a) menthol with
b) a quantity of menthane carboxylic acid-N-(4-methoxyphenyl)-amide (WS-12) that masks the bitterness of the menthol, c) one, two or more further flavoring agents, wherein the, a plurality or all of the further flavoring agents have a log-$K_{ow}$ value in the range of 1.5-5 and the quantity used of these further flavoring agents is selected so that the solubility of the menthane carboxylic acid-N-(4-methoxyphenyl)-amide (WS-12) is increased, and
d) further teeth cleaning components.

It is self-evident that, concerning the method according to the invention, the preferred embodiments discussed above with a view to the teeth cleaning compound according to the invention apply accordingly.

In the following the present invention is explained in more detail by the use of examples, wherein the examples that follow do not limit the invention.

Unless otherwise stated, here all (stated) quantities refer to the weight.

BRIEF DESCRIPTION OF THE DRAWINGS

FIG. 1 shows the intensity and duration of the cooling sensation of freshness of toothpastes containing a flavoring agent composition according to a) Example 1.2 ($1^{st}$ formulation) with menthane-3-carboxylic acid-N-ethyl amide (WS-3)—represented by a continuous line with hash marks—or according to b) Example 1.2 ($1^{st}$ preparation) with menthane-3-carboxylic acid-N-(4-methoxyphenyl)-amide (WS-12)—represented by a broken line with squares. The abscissa of FIG. 1 gives the time in minutes elapsing since cleaning of the teeth with the respective toothpaste.

EXAMPLES

In the following examples various essential oils are used. For the calculation of the overall proportion of menthol and the proportion of the one, two, or more further flavoring agents with a log-$K_{ow}$ value in the range of 1.5-5 in the respective flavoring agent composition (ii), the following proportions in the essential oils used are used as a basis:

Peppermint oil, *Mentha arvensis*, rectified (commercial dementholized grade): 1,8-cineole (eucalyptol) approximately 0.4%; menthone approximately 35%; menthol approximately 40%.

Peppermint oil, *Mentha piperita*, Willamette type: 1,8-cineole (eucalyptol) approximately 5%; menthone approximately 30%; menthol approximately 40%.

Spearmint oil, native type: 1,8-cineole (eucalyptol) approximately 2.2%; carvone approximately 70%.

Spearmint oil, Midwest Scotch type: 1,8-cineole (eucalyptol) approximately 1.5%; carvone approximately 70%.

In the following examples, where peppermint oil is used this is the native type. In place of native type spearmint oil, the use of the Midwest Scotch type is also advantageous. The content calculations of the examples concerned with spearmint oil refer to figures given for content of native type spearmint oil.

In a few examples a pellitorine solution (referred to in the following as "pellitorine solution PLM") is used, consisting of 10% pellitorine (comprising 4.9% 2E,4Z-decadienoic acid-N-isobutyl amide and 94.3% 2E,4E-decadienoic acid-N-isobutyl amide and 0.8% solvent), 45% propylene glycol and 45% natural peppermint oil (*Mentha arvensis*, rectified).

Example 1

Teeth Cleaning Compound Containing a Flavoring Agent Composition of the Eucalyptus-menthol-type—Comparative Investigations

Example 1.1

Reduction of the Bitter Note of Menthol in Teeth Cleaning Compounds Through a Proportion of Anethole (Comparative Example)

$1^{st}$ Formulation:

The following were mixed together:
20 wt. % peppermint oil *Mentha piperita*, Willamette type
20 wt. % peppermint oil *Mentha arvensis*, rectified
1 wt. % I-menthyl acetate
2 wt. % 2-hydroxyethylmenthyl carbonate
2 wt. % 2-hydroxypropylmenthyl carbonate
5 wt. % 1,8-cineole (eucalyptol)
40 wt. % I-menthol
10 wt. % anethole $2^{nd}$ Formulation:

In the $2^{nd}$ formulation the components of the $1^{st}$ formulation were mixed together in the same proportions, but without anethole.

The flavoring agent compositions obtained in this way were in each case incorporated into a respective standard toothpaste mass with a silicic acid basis in a concentration of 1.2 wt. %, in relation to the overall weight of the resulting toothpaste. The toothpastes were tested by a panel of sensorially trained experts under usage conditions. The sensorial assessment revealed that despite the high content of menthol in the flavoring agent composition (56 wt. % overall menthol content, of which 40 wt. % was linearly added menthol) through the use of 10 wt. % anethole in the $1^{st}$ formulation, the bitter-sharp note of the menthol was neutralized and thus overall a pleasant taste result was achieved. Without the use of anethole in the $2^{nd}$ formulation the bitter-sharp note clearly emerged and the taste result was perceived overall to be unacceptable.

Example 1.2

Reduction of the Bitter Note of Menthol in Teeth Cleaning Compounds Through a Proportion of menthane carboxylic acid-N-(4-methoxyphenyl)-amide (WS-12)

$1^{st}$ Formulation

The following were mixed together:
25 wt. % peppermint oil, *Mentha piperita*, Willamette type
25 wt. % peppermint oil, *Mentha arvensis*, rectified
1 wt. % I-menthyl acetate
2 wt. % 2-hydroxyethylmenthyl carbonate
2 wt. % 2-hydroxypropylmenthyl carbonate
5 wt. % 1,8-cineole (eucalyptol)
39.5 wt. % I-menthol
0.5 wt. % menthane carboxylic acid-N-(4-methoxyphenyl)-amide $2^{nd}$ Formulation:

In a $2^{nd}$ formulation the constituents of the $1^{st}$ formulation were mixed together in the same proportions but without menthane carboxylic acid-N-(4-methoxyphenyl)-amide (WS-12).

The flavoring agent compositions obtained in this way were in each case incorporated into a respective standard toothpaste mass with a silicic acid basis in a concentration of 1.2 wt. %, in relation to the overall weight of the resulting toothpaste. The toothpastes were tested by a panel of sensorially trained experts under usage conditions. The sensorial assessment revealed that with the use of 0.5 wt. % menthane carboxylic acid-N-(4-methoxyphenyl)-amide (WS-12) in the $1^{st}$ preparation the bitter-sharp note of the menthol (compared to the $2^{nd}$ formulation) was significantly reduced and the toothpaste was perceived to be aromatically fuller and more rounded. The flavoring agent composition or the toothpaste exhibited a very pleasant, richly minty freshness with a very strong and distinctive, long-lasting cooling sensation of freshness.

Without the use of menthane carboxylic acid-N-(4-methoxyphenyl)-amide (WS-12) the bitter-sharp note of the menthol clearly emerged and the aroma was perceived as significantly less pleasant. The impression of a cooling sensation of freshness also lasted for significantly less time.

In the flavoring agent composition described above according to the $1^{st}$ formulation (Example 2.2), the proportion of linearly added menthol is 40 wt. % (with an overall menthol content—as a result of the menthol also contained in the peppermint oils—of 59.5 wt. %). The weight ratio of menthane carboxylic acid-N-(4-methoxyphenyl)-amide (WS-12) to linearly added menthol is thus 1:80. The weight ratio of menthane carboxylic acid-N-(4-methoxyphenyl)-amide (WS-12) to the overall quantity of menthol is 1:119. The weight ratio of menthane carboxylic acid-N-(4-methoxyphenyl)-amide (WS-12) to the overall quantity of further flavoring agents with a log-$K_{ow}$ value in the range of 1.5-5 (1-menthyl acetate, 1,8-cineole, and the abovementioned corresponding proportions of peppermint oils) is 1:47.

Example 2

Prolonging the Cooling Sensation of Freshness Brought About by a Teeth Cleaning Compound Through the use of menthane carboxylic acid-N-(4-methoxyphenyl)-amide (WS-12)

The proportion of menthane carboxylic acid-N-(4-methoxyphenyl)-amide (WS-12) in the $1^{st}$ preparation of Example 1.2 was replaced by menthane-3-carboxylic acid-N-ethyl amide (WS-3).

The flavoring agent composition obtained was likewise incorporated into a standard toothpaste mass with a silicic acid base in a concentration of 1.2 wt. %, in relation to the overall weight of the resultant toothpaste.

The toothpaste prepared in this way was tested by a panel of sensorially trained experts under usage conditions and compared with the toothpaste containing menthane carboxylic acid-N-(4-methoxyphenyl)-amide (WS-12) according to the $1^{st}$ formulation of Example 1.2 in respect of the bitter perception and the duration of the cooling sensation of freshness.

In the case of the toothpaste with the flavoring agent composition containing menthane-3-carboxylic acid-N-ethyl amide (WS-3), the bitter perception was hardly reduced, whereas in the case of the toothpaste containing the flavoring agent composition with menthane carboxylic acid-N-(4-methoxyphenyl)-amide (WS-12), the bitter perception was significantly reduced. In addition the toothpaste with menthane carboxylic acid-N-(4-methoxyphenyl)-amide (WS-12) was perceived as aromatically more harmonic, rounder and fuller. This impression was supported by the comparatively long-lasting sensation of freshness which was triggered by the use of menthane carboxylic acid-N-(4- methoxyphenyl)-amide (WS-12). The behavior over time of the cooling sensation of freshness is illustrated in FIG. 1.

FIG. 1 shows the intensity and duration of the cooling sensation of freshness of toothpastes containing a flavoring agent composition according to a) Example 1.2 (1$^{st}$ formulation) with menthane-3-carboxylic acid-N-ethyl amide (WS-3)—represented by a continuous line with hash marks—or according to b) Example 1.2 (1$^{st}$ preparation) with menthane-3-carboxylic acid-N-(4-methoxyphenyl)-amide (WS-12)—represented by a broken line with squares. The abscissa of FIG. 1 gives the time in minutes elapsing since cleaning of the teeth with the respective toothpaste.

The ordinate of FIG. 1 shows the intensity of coolness perceived. The intensity of coolness perceived was rated on a scale of 0 to 10, with a value of "0" corresponding to the lowest or no intensity of coolness perceived and a value of "8" corresponding to the highest intensity of coolness perceived.

It can be seen immediately from FIG. 1 that the toothpaste containing a flavoring agent composition with menthane-3-carboxylic acid-N-(4-methoxyphenyl)-amide (WS-12) compared to the toothpaste containing a flavoring agent composition with menthane-3-carboxylic acid-N-ethyl amide (WS-3) imparts a considerably longer sensation of freshness. After 35 minutes the toothpaste containing a flavoring agent composition with menthane-3-carboxylic acid-N-ethyl amide (WS-3), with a value of "0", had little or no more intensity of coolness perceived, whereas with the toothpaste containing a flavoring agent composition with menthane-3-carboxylic acid-N-(4-methoxyphenyl)-amide (WS-12) after 35 minutes an intensity of coolness with a value of "3" was perceived which even after 60 minutes still had a value of between "1" and "2" (approximately "1.5").

Example 3

Toothpaste with No or Only a Slight Bitter Taste Containing a Flavoring Agent Composition with High Menthol Content and Cinnamon Flavor For the production of a flavoring agent composition the following were mixed together:
5 wt. % cinnamaldehyde
22.5 wt. % peppermint oil, *Mentha piperita*, Willamette type
22.5 wt. % peppermint oil, *Mentha arvensis*, rectified
1 wt. % I-menthyl acetate
2 wt. % 2-hydroxyethylmenthyl carbonate
2 wt. % 2-hydroxypropylmenthyl carbonate
5 wt. % 1,8-cineole (eucalyptol)
39.5 wt. % I-menthol
0.5 wt. % menthane carboxylic acid-N-(4-methoxyphenyl)-amide.

The flavoring agent composition obtained in this way was incorporated into a standard toothpaste mass with a silicic acid base in a concentration of 1.2 wt. %, in relation to the overall weight of the resulting toothpaste. The toothpaste was tested by a panel of sensorially trained experts under usage conditions. The sensorial assessment revealed that despite the high content of menthol the bitter note was sharply reduced. Since through the use of menthane carboxylic acid-N-(4-methoxyphenyl)-amide (WS-12) in combination with the further flavoring agents with a log-K$_{ow}$ value in the range of 1.5-5 (I-menthyl acetate, 1,8-cineole, cinnamaldehyde, and abovementioned corresponding proportions of peppermint oils) a strong reduction in bitterness (of the menthol) was achieved, it was advantageously possible to dispense with the use of anethole to reduce the bitterness. Apart from a pleasant, distinctly fresh, long-lasting taste impression, the toothpaste was also able to impart a distinct, sweet cinnamon note as a result of the proportion of cinnamaldehyde.

In the above flavoring agent composition, the proportion of linearly added menthol is 39.5 wt. % (for an overall menthol content—as a result of the menthol also contained in the peppermint oils—of 57.5 wt. %). The weight ratio of menthane carboxylic acid-N-(4-methoxyphenyl)-amide (WS-12) to linearly added menthol is thus 1:79. The weight ratio of menthane carboxylic acid-N-(4-methoxyphenyl)-amide (WS-12) to the overall quantity of menthol is 1:115. The weight ratio of menthane carboxylic acid-N-(4-methoxyphenyl)-amide (WS-12) to the overall quantity of the further flavoring agents with a log-K$_{ow}$ value in the range of 1.5-5 (I-menthyl acetate, 1,8-cineole, cinnamaldehyde, and abovementioned corresponding proportions of peppermint oils) is 1:54.

Example 4

Teeth Cleaning Compound Containing a Flavoring Agent Composition with Spearmint Character—Comparative Investigations Example 4.1 (Comparative Example)

Through the mixing together of

| 30 | wt. % | Menthol |
|---|---|---|
| 20 | wt. % | Carvone |
| 20 | wt. % | Native type spearmint oil |
| 5 | wt. % | Anethole |
| 10 | wt. % | Peppermint oil, *Mentha arvensis*, rectified |
| 15 | wt. % | Peppermint oil, *Mentha piperita*, Willamette type | a flavoring agent composition for teeth cleaning compounds with a spearmint character was produced.

Example 4.2

Through the mixing together of

| 39.5 | wt. % | Menthol |
|---|---|---|
| 20 | wt. % | Carvone |
| 20 | wt. % | Native type spearmint oil |
| 10 | wt. % | Peppermint oil, *Mentha arvensis*, rectified |
| 10 | wt. % | Peppermint oil, *Mentha piperita*, Willamette type |
| 0.5 | wt. % | Menthane carboxylic acid-N-(4-methoxyphenyl)-amide | a flavoring agent composition with a proportion of 0.5 wt. % of menthane carboxylic acid-N-(4-methoxyphenyl)-amide (WS-12) for teeth cleaning compounds with spearmint character was produced.

The flavoring agent compositions according to Example 4.1 (for a teeth cleaning compound for comparative purposes) and Example 4.2 (for a teeth cleaning compound according to the invention) were in each case incorporated with a concentration of 1.2 wt. %, in relation to the overall weight of the resulting toothpaste into a respective toothpaste mass, containing a proportion of 65 wt. % sodium bicarbonate.

The resulting toothpastes were tested under usage conditions and rated by a panel of sensorially trained experts. The sensorial assessment for the toothpaste (according to the invention) containing a flavoring agent composition according to Example 4.2 revealed a very powerful, pleasant, fresh-mint spearmint flavor coupled with a long-lasting sensation of freshness. Compared with the toothpaste with the flavoring agent composition according to Example 4.1, i.e. without menthane carboxylic acid-N-(4-methoxyphenyl)-amide (WS-12), but with anethole, the sensation of freshness with the toothpaste containing a flavoring agent composition according to Example 4.2 was considerably reinforced and in this way the typical spearmint character considerably emphasized. Through the proportion of 0.5 wt. % of menthane carboxylic acid-N-(4-methoxyphenyl)-amide (WS-12) in the flavoring agent composition according to Example 4.2 the proportion of 5 wt. % of anethole used to reduce the bitterness in Example 4.1 was no longer needed to reduce the bitterness of the menthol. The quantity of menthane carboxylic acid-N-(4-methoxyphenyl)-amide (WS-12) used was sufficient for the purposes of reducing the bitterness. In addition, it was possible to advantageously increase the linearly added proportion of menthol in the flavoring agent composition from 30 wt. % (Example 4.1) to 39.5 wt. % (Example 4.2), without a bitter-sharp note of the menthol arising as would have been expected with a flavoring agent composition according to Example 4.1 with such an increased proportion of linearly added menthol.

In the flavoring agent composition according to Example 4.2 described above, the proportion of linearly added menthol is 39.5 wt. % (for an overall menthol content—due to the additional menthol contained in the peppermint oils—of 47.5 wt. %). The weight ratio of menthane carboxylic acid-N-(4-methoxyphenyl)-amide (WS-12) to linearly added menthol is thus 1:79. The weight ratio of menthane carboxylic acid-N-(4-methoxyphenyl)-amide (WS-12) to the overall quantity of menthol is 1:95.

The weight ratio of menthane carboxylic acid-N-(4-methoxyphenyl)-amide (WS-12) to the overall quantity of further flavoring agents with a log-$K_{ow}$ value in the range of 1.5-5 (carvone, and the abovementioned corresponding proportions of peppermint oils and of the spearmint oil) is 1:83.

Example 5

Teeth Cleaning Compound Containing a Flavoring Agent Composition with a Spicy Aromatic Note—Comparative Investigations Example 5.1 (Comparative Example)

Through the mixing together of

| | | |
|---|---|---|
| 30 | wt. % | l-menthol |
| 25 | wt. % | Peppermint oil, *Mentha arvensis*, rectified |
| 15 | wt. % | Peppermint oil, *Mentha piperita*, Willamette type |
| 10 | wt. % | Anethole |
| 10 | wt. % | Native type spearmint oil |
| 5 | wt. % | Cinnamaldehyde |
| 5 | wt. % | Eugenol | a flavoring agent composition for teeth cleaning compounds with a spicy aromatic note was produced.

Example 5.2

Through the mixing together of

| | | |
|---|---|---|
| 40 | wt. % | l-menthol |
| 22 | wt. % | Peppermint oil, *Mentha arvensis*, rectified |
| 12.5 | wt. % | Peppermint oil, *Mentha piperita*, Willamette type |
| 5 | wt. % | Anethole |
| 10 | wt. % | Native type spearmint oil |

-continued

| | | |
|---|---|---|
| 5 | wt. % | Cinnamaldehyde |
| 5 | wt. % | Eugenol |
| 0.5 | wt. % | Menthane carboxylic acid-N-(4-methoxyphenyl)-amide | a flavoring agent composition with a proportion of 0.5 wt. % menthane carboxylic acid-N-(4-methoxyphenyl)-amide (WS-12) for teeth cleaning compounds with a spicy aromatic note was produced.

The flavoring agent compositions according to Example 5.1 (for a teeth cleaning compound for comparative purposes) and Example 5.2 (for a teeth cleaning compound according to the invention) were in each case incorporated in concentration of 1.2 wt. % into a respective standard toothpaste mass with a silicic acid base, in relation to the overall weight of the resulting toothpaste.

The resulting toothpastes were tested under usage conditions and rated by a panel of sensorially trained experts. The sensorial assessment for the toothpaste (according to the invention) containing a flavoring agent composition according to Example 5.2 revealed a marked minty fresh-aromatic taste note with a very strong and distinctive, very long-lasting, cooling sensation of freshness.

Through the proportion of 0.5 wt. % menthane carboxylic acid-N-(4-methoxyphenyl)-amide (WS-12) in the flavoring agent composition according to Example 5.2 it was possible to reduce the proportion of anethole used in Example 5.1 to reduce the bitterness from 10 wt. % to 5 wt. %. In addition, it was possible to increase the linearly added proportion of menthol in the flavoring agent composition from 30 wt. % (Example 5.1) to 40 wt. % (Example 5.2), without a bitter-sharp note of the menthol arising as would have been expected with a flavoring agent composition according to Example 5.1 with such an increased proportion of linearly added menthol.

In the flavoring agent composition according to Example 5.2 described above, the proportion of linearly added menthol is 40 wt. % (for an overall menthol content—due to the additional menthol contained in the peppermint oils—of 53.8 wt. %). The weight ratio of menthane carboxylic acid-N-(4-methoxyphenyl)-amide (WS-12) to linearly added menthol is thus 1:80. The weight ratio of menthane carboxylic acid-N-(4-methoxyphenyl)-amide (WS-12) to the overall quantity of menthol is 1:108.

The weight ratio of menthane carboxylic acid-N-(4-methoxyphenyl)-amide (WS-12) to the overall quantity of further flavoring agents with a log-$K_{ow}$ value in the range of 1.5-5 (anethole, cinnamaldehyde, and the abovementioned corresponding proportions of the peppermint oils and of the spearmint oil) is 1:59.

Example 6

Teeth Cleaning Compound Comprising a Flavoring Agent Composition with a Wintergreen Character—Comparative Investigations Example 6.1 (Comparative Example)

Through the mixing together of

| | | |
|---|---|---|
| 10 | wt. % | Anethole |
| 12.5 | wt. % | Peppermint oil, *Mentha arvensis*, rectified |
| 12.5 | wt. % | Peppermint oil, *Mentha piperita*, Willamette type |

| | | |
|---|---|---|
| 25 | wt. % | Methyl salicylate |
| 40 | wt. % | l-menthol | a flavoring agent composition for teeth cleaning compounds with a wintergreen character was produced.

Example 6.2

Through the mixing together of:

| | | |
|---|---|---|
| 17 | wt. % | Peppermint oil, *Mentha arvensis*, rectified |
| 17.5 | wt. % | Peppermint oil, *Mentha piperita*, Willamette type |
| 25 | wt. % | Methyl salicylate |
| 40 | wt. % | l-menthol |
| 0.5 | wt. % | Menthane carboxylic acid-N-(4-methoxyphenyl)-amide | a flavoring agent composition with a proportion of 0.5 wt. % menthane carboxylic acid-N-(4-methoxyphenyl)-amide (WS-12) for teeth cleaning compounds with a wintergreen character was produced.

The flavoring agent compositions according to Example 6.1 (for a teeth cleaning compound for comparative purposes) and Example 6.2 (for a teeth cleaning compound according to the invention) were in each case incorporated into a respective standard toothpaste mass with a silicic acid base with a concentration of 1.2 wt. % in relation to the overall weight of the resulting toothpaste.

The resulting toothpastes were tested under usage conditions and rated by a panel of sensorially trained experts. The sensorial assessment for the toothpaste containing a flavoring agent composition according to Example 6.2 revealed a marked fresh-peppermint wintergreen note with a very strong and distinctive, very long-lasting, cooling sensation of freshness. Through the proportion of 0.5 wt. % of menthane carboxylic acid-N-(4-methoxyphenyl)-amide (WS-12) in the flavoring agent composition according to Example 6.2, the proportion of anethole (10 wt. %) used to reduce the bitterness in Example 6.1 was no longer needed to reduce the bitterness of the menthol. In addition, it was advantageously possible to increase the (overall) proportion of menthol in the flavoring agent composition by raising the wt. % proportions of the peppermint oil *Mentha arvensis*, rectified, from 12.5 wt. % (Example 6.1) to 17 wt. % (Example 6.2) and of the peppermint oil *Mentha piperita*, Willamette type, from 12.5 wt. % (Example 6.1) to 17.5 wt. % (Example 6.2), without the bitter sharp note of the menthol occurring.

In the flavoring agent composition according to Example 6.2 described above, the proportion of linearly added menthol is 40 wt. % (for an overall menthol content—due to the additional menthol contained in the peppermint oils—of 54 wt. %). The weight ratio of menthane carboxylic acid-N-(4-methoxyphenyl)-amide (WS-12) to linearly added menthol is thus 1:80. The weight ratio of menthane carboxylic acid-N-(4-methoxyphenyl)-amide (WS-12) to the overall quantity of menthol is 1:108.

The weight ratio of menthane carboxylic acid-N-(4-methoxyphenyl)-amide (WS-12) to the overall quantity of further flavoring agents with a log-$K_{ow}$ value in the range of 1.5-5 (methyl salicylate, and the abovementioned corresponding proportions of the peppermint oils) is 1:74.

Example 7

Mouthwash or Mouthwash Concentrate Containing a Flavoring Agent Composition with a Eucalyptus Character—Comparative Investigations Example 7.1 (Comparative Example)

Through the mixing together of

| | | |
|---|---|---|
| 30 | wt. % | Anethole |
| 25 | wt. % | 1,8-cineole (eucalyptol) |
| 45 | wt. % | l-menthol | a flavoring agent composition for use in mouthwashes or mouthwash concentrates was produced.

Example 7.2

Through the mixing together of

| | | |
|---|---|---|
| 10 | wt. % | Anethole |
| 17.5 | wt. % | *Eucalyptus* oil (70-75% 1,8-cineole) |
| 17.5 | wt. % | 1,8-cineole (eucalyptol) |
| 54.4 | wt. % | l-menthol |
| 0.6 | wt. % | Menthane carboxylic acid-N-(4-methoxyphenyl)-amide | a flavoring agent composition with a proportion of 0.6 wt. % menthane carboxylic acid-N-(4-methoxyphenyl)-amide (WS-12) for use in mouthwashes or mouthwash concentrates was produced.

The flavoring agent compositions according to Example 7.1 (for a mouth wash for comparative purposes or a mouthwash concentrate for comparative purposes) and Example 7.2 (for a mouthwash according to the invention or a mouthwash concentrate according to the invention) were incorporated in each case with a concentration of 0.15 wt. % in each case into a ready-to-use mouthwash or in each case with a concentration of 3 wt. % in each case into a ready-to-use mouthwash concentrate, in relation to the overall weight of the resultant mouthwash or of the resultant mouthwash concentrate.

The resultant mouthwashes or mouthwash concentrates were tested under usage conditions by a sensorially trained panel of experts. The sensorial assessment for the mouthwash/mouthwash concentrate containing a flavoring agent composition according to Example 7.2 revealed a strong, pleasantly fresh eucalyptus note with a very long-lasting sensation of freshness which even after the use of the mouthwash/mouthwash concentrate lasted for well over 30 minutes.

Through the proportion of 0.6 wt. % of menthane carboxylic acid-N-(4-methoxyphenyl)-amide (WS-12) in the flavoring agent composition according to Example 7.2, now it was possible to reduce the proportion of anethole (30 wt. %) used to reduce the bitterness in Example 7.1 to 10 wt. %. In addition, it was possible to increase the linearly added proportion of menthol in the flavoring agent composition from 40 wt. % (Example 7.1) to 54.4 wt. % (Example 7.2). At the same time it was possible to add 17.5 wt. % of eucalyptus oil (comprising 70-75% 1,8-cineole), without the bitter-sharp note of the menthol occurring.

In the flavoring agent composition according to Example 7.2 described above, the proportion of the linearly added menthol is 54.4 wt. %, corresponding to the overall proportion of menthol. The weight ratio of menthane carboxylic acid-N-(4-methoxyphenyl)-amide (WS-12) to linearly added menthol or to the overall menthol content is thus 1:91.

The weight ratio of menthane carboxylic acid-N-(4-methoxyphenyl)-amide (WS-12) to the overall quantity of further flavoring agents with a log-$K_{ow}$ value in the range of 1.5-5 (anethole, 1,8-cineole, and corresponding proportion of 1,8-cineole in the eucalyptus oil) is 1:68-1:70, according to the proportion of 1,8-cineole in the eucalyptus oil.

Further Application Examples of Flavoring Agent Compositions Described Above in Finished Products:

The flavoring agent compositions described in examples 1 to 7 are suitable not only for use in toothpastes, but also for use in a whole range of further, different finished products. In all the application examples given in the following it has been possible (in our own tests) to perceive an advantageous, rapidly occurring and simultaneously long-lasting sensation of freshness, without this sensation of freshness being adversely affected by bitter and/or (undesired) sharp notes, which may arise through the presence of menthol or also through other substances with a bitter and/or (undesired) sharp note.

Example 8

Toothpaste ('Silica Opaque')

| Ingredient | I (wt. %) | II (wt. %) |
|---|---|---|
| Deionized water | 26.53 | 26.53 |
| Sorbitol 70% | 45.00 | To 100 |
| Solbrol M Na-salt | 0.15 | 0.15 |
| Trisodium phosphate | 0.10 | 0.10 |
| Saccharin | 0.20 | 0.20 |
| Sodium monofluorophosphate | 1.12 | 1.12 |
| PEG 1500 | 5.00 | 5.00 |
| Sident 9 (abrasive silica) | 10.00 | 10.00 |
| Sident 22 S (thickening silica) | 8.00 | 8.00 |
| Sodium carboxymethyl cellulose | 0.90 | 0.90 |
| Titanium (IV) oxide | 0.50 | 0.50 |
| Sodium Lauryl Sulfate (SLS) | 1.50 | 1.50 |
| Pellitorine solution PLM (containing 10% pellitorine) | — | 0.025 |
| *Eucalyptus*-menthol type flavor (Example 2.2) | 1.00 | 1.00 |

Example 9

Toothpaste (Calcium Carbonate Base)

| Ingredient | I (wt. %) | II (wt. %) |
|---|---|---|
| Deionized water | 27.50 | To 100 |
| Saccharin | 0.20 | 0.20 |
| Solbrol M sodium salt | 0.20 | 0.20 |
| Sodium monofluorophosphate | 0.80 | 0.80 |
| Sorbitol 70% | 29.00 | 29.00 |
| Calcium carbonate | 35.00 | 35.00 |
| Sident 22 S (thickening silica) | 2.50 | 2.50 |
| Sodium carboxymethyl cellulose | 1.30 | 1.30 |
| Titanium dioxide | 0.50 | 0.50 |
| Sodium lauryl sulfate | 2.00 | 2.00 |
| *Eucalyptus*-menthol type flavor (Example 2.2) | 1.00 | 1.00 |
| Pellitorine solution PLM (containing 10% pellitorine) | — | 0.020 |

Example 10

Bleaching Toothpaste

| | I (wt. %) | II (wt. %) | III (wt. %) |
|---|---|---|---|
| Polyphosphate (Glass H, (n ≈ 21), *Astaris*) | 7.00 | 7.00 | 7.00 |
| Calcium peroxide | 1.00 | — | 2.50 |
| Na-percarbonate | — | 11.00 | — |
| Poloxamer 407 | 5.00 | 2.00 | 5.00 |
| Polyethylene glycol | 3.00 | — | 3.00 |
| Sorbitol, 70% in water | — | 22.00 | — |
| Glycerin | 43.80 | 12.50 | 28.60 |
| 1,2-propylene glycol | 4.00 | — | 2.50 |
| Na-saccharin | 0.40 | 0.20 | 0.50 |
| Sodium bicarbonate | — | 5.00 | 15.00 |
| Sodium carbonate | 2.00 | 2.00 | 2.00 |
| Silica | 20.00 | 22.00 | 20.00 |
| Na-carboxymethylcellulose | 0.60 | 0.55 | 0.30 |
| Sodium lauryl sulfate | 1.00 | 4.00 | 2.00 |
| Xanthan gum | 0.20 | 0.20 | 0.20 |
| Titanium dioxide (*Anatas*) | 0.50 | 0.50 | 0.50 |
| *Eucalyptus* menthol type flavor (Example 2.2) | 1.00 | — | — |
| Menthol cinnamon type flavor (Example 4) | — | 1.25 | — |
| Cinnamon spicy flavor (Example 6.2) | — | — | 1.50 |
| Distilled water | To 100 | To 100 | To 100 |

Example 11

Toothpastes with Tin and Zinc Salts

| | I (wt. %) | II (wt. %) | III (wt. %) |
|---|---|---|---|
| Sodium fluoride NaF | 0.42 | 0.50 | — |
| Tin fluoride $SnF_2$ | — | 0.90 | 0.95 |
| Tin chloride $SnCl_2$ | 1.50 | — | 2.00 |
| Zinc lactate | 2.00 | 2.00 | — |
| Zinc carbonate $ZnCO_3$ | — | 1.00 | 1.50 |
| Na-gluconate | — | 0.67 | 1.50 |
| Poloxamer 407 | 14.50 | — | — |
| Polyethylene glycol | 1.00 | 3.00 | — |
| Sorbitol, 70% in water | — | 38.00 | 37.50 |
| Glycerin | 37.50 | 5.00 | 14.40 |
| 1,2-propylene glycol | 7.00 | 5.00 | — |
| Na-saccharin | 0.30 | 0.50 | 0.50 |
| Abrasive silica | 20.00 | 22.50 | 25.00 |
| Sodium hydroxide | — | 0.10 | 0.20 |
| Sodium lauryl sulfate | — | 2.00 | 1.50 |
| Na-polyphosphate | — | — | 4.00 |
| Tetrasodium pyrophosphate | 1.00 | 2.50 | — |
| Coloring (1% in water) | 0.40 | 0.50 | 0.50 |
| *Eucalyptus* menthol type flavor (Example 2.2) | 0.95 | — | — |
| Menthol cinnamon type flavor (Example 4) | — | 1.20 | — |
| Wintergreen flavor (Example 7.2) | — | — | 1.15 |
| Distilled water | To 100 | To 100 | To 100 |

Example 12

Phosphate Based Toothpaste

| Ingredient | Proportion [%] |
|---|---|
| Deionized water | 36.39 |
| Glycerin | 20.00 |
| Solbrol M (sodium salt) | 0.15 |
| Sodium monofluorophosphate | 0.76 |
| Saccharin | 0.20 |
| Dicalcium phosphate dihydrate | 36.00 |

-continued

| Ingredient | Proportion [%] |
|---|---|
| Aerosil ® 200 (Silica) | 3.00 |
| Sodium carboxymethyl cellulose | 1.20 |
| Sodium lauryl sulfate (Texapon) | 1.30 |
| Spearmint type flavor (Example 5.2) | 1.00 |

Example 13

Toothpaste (Transparent Gel Formulation)

| Ingredient | I (wt. %) | II (wt. %) |
|---|---|---|
| Sorbitol 70% | 63.00 | To 100 |
| Deionized water | 11.31 | 11.31 |
| Saccharin | 0.20 | 0.20 |
| Sodium monofluorophosphate | 1.14 | 1.14 |
| Solbrol | 0.15 | 0.15 |
| Trisodium phosphate | 0.10 | 0.10 |
| PEG 1500 (PEG 32) | 5.00 | 5.00 |
| Sident 9 (abrasive silica) | 8.00 | 8.00 |
| Sident 22 S (thickening silica) | 8.00 | 8.00 |
| Sodium carboxymethyl cellulose | 0.60 | 0.60 |
| Sodium lauryl sulfate | 1.50 | 1.50 |
| Menthol cinnamon type flavor (Example 4) | 1.00 | — |
| Wintergreen flavor (Example 7.2) | — | 1.00 |
| Pellitorine solution PLM (containing 10% Pellitorine) | — | 0.025 |

Example 14

Tooth Crème and Mouthwash as a 2-in-1 Product

| | I (wt. %) |
|---|---|
| Ethanol, 96% | 5.00 |
| Sorbitol, 70% in water | 40.00 |
| Glycerin | 20.00 |
| Saccharin | 0.20 |
| Na-monofluorophosphate | 0.76 |
| Solbrol M, Na-salt | 0.15 |
| Abrasive silica (Sident 9) | 20.00 |
| Thickening silicic acid (Sident 22S) | 2.00 |
| Na-carboxymethylcellulose | 0.30 |
| Sodium lauryl sulfate | 1.20 |
| Green coloring (1% in water) | 0.50 |
| *Eucalyptus* menthol type flavor (Example 2.2) | 1.00 |
| Distilled water | To 100 |

Example 15

Mouthwash Concentrate Containing a Flavoring Agent Composition of the Wintergreen Type

| Ingredient | Proportion [%] |
|---|---|
| Ethyl alcohol 96% | 42.00 |
| Cremophor RH 455 | 5.00 |
| Deionized water | 48.67 |
| Allantoin | 0.20 |
| Sodium saccharin 450 | 0.10 |
| Color L-Blue 5000 (1% in water) | 0.03 |
| Wintergreen flavor (Example 7.2) | 4.00 |

Example 16

Mouthwash ('Ready to Use', Alcohol-free)

| Ingredient | I (wt. %) | II (wt. %) |
|---|---|---|
| Cremophor RH 455 | 1.80 | 1.80 |
| Deionized water | 87.57 | To 100 |
| Sorbitol 70% | 10.00 | 10.00 |
| Sodium fluoride | 0.18 | 0.18 |
| Sodium saccharin 450 | 0.10 | 0.10 |
| Solbrol M sodium salt | 0.15 | 0.15 |
| *Eucalyptus* menthol type flavor (Example 2.2) | 0.2 | 0.2 |
| Pellitorine solution PLM (containing 10% pellitorine) | — | 0.0125 |

Example 17

Mouthwash ('Ready to Use', with Alcohol)

| Ingredient | I (wt. %) | II (wt. %) | III (wt. %) |
|---|---|---|---|
| Ethyl alcohol 96% | 10.02 | 5.00 | 7.00 |
| Cremophor CO 40 | 1.00 | 1.00 | 1.00 |
| Benzoic acid | 0.10 | 0.12 | 0.10 |
| Deionized water | 83.46 | To 100 | To 100 |
| Sorbitol 70% | 5.00 | 1.00 | 5.00 |
| Sodium saccharin 450 | 0.07 | 0.05 | 0.05 |
| L-Blue 5000 (1% in water) | 0.10 | 0.10 | 0.10 |
| Glycerin | — | 8.00 | — |
| 1,2-propylene glycol | — | 2.00 | 3.00 |
| Cetylpyridinium chloride | — | — | 0.07 |
| Hydrogen peroxide (35% $H_2O_2$ in water) | — | 3.00 | 4.00 |
| Wintergreen flavor (Example 7.2) | 0.25 | — | — |
| *Eucalyptus* menthol type flavor (Example 2.2) | — | 0.25 | 0.05 |

Example 18

Standard Chewing Gum

| Ingredient | I (wt. %) | II (wt. %) |
|---|---|---|
| Gum base (chewing gum base) | 21.00 | 21.00 |
| Glucose syrup | 16.50 | 16.50 |
| Glycerin | 0.50 | 0.50 |
| Powdered sugar | 60.00 | 60.00 |
| *Eucalyptus* menthol type flavor (Example 2.2) | 2.00 | — |
| Spearmint type flavor (Example 5.2) | — | 2.00 |

Example 19

Sugar-free Chewing Gum

| Ingredient | I (wt. %) | II (wt. %) |
|---|---|---|
| Gum base (chewing gum base) | 30.00 | 30.00 |
| Powdered sorbitol | 40.00 | To 100 |
| Powdered isomaltitol | 9.50 | 9.50 |
| Xylitol | 2.00 | 2.00 |
| Mannitol D | 3.00 | 3.00 |
| Aspartame | 0.10 | 0.10 |
| Acesulfame K | 0.10 | 0.10 |
| Emulgum ™ (soya-lecithin with a high content of phospholipids) | 0.30 | 0.30 |
| Sorbitol (70% in water) | 13.00 | 13.00 |
| 1,2-propylene glycol | — | 1.00 |
| Glycerin | 1.00 | — |
| Pellitorine solution PLM (containing 10% pellitorine) | — | 0.035 |
| Menthol cinnamon type flavor (Example 4) | 1.00 | 1.00 |

Example 20

Chewing Gum (with Sugar and Sugar-free)

| | I (wt. %) | II (wt. %) |
|---|---|---|
| Gum Base (chewing gum base) | 21.0 | 30.0 |
| Glycerin | 0.5 | 1.0 |
| Spearmint type flavor (Example 5.2) | 1.0 | 1.4 |
| Glucose syrup | 16.5 | — |
| Powdered sugar | To 100 | — |
| Sorbitol (in in powder form) | — | To 100 |
| Palatinite | — | 9.5 |
| Xylitol | — | 2.0 |
| Mannitol | — | 3.0 |
| Aspartame | — | 0.1 |
| Acesulfame K | — | 0.1 |
| Emulgum ™ (emulsifier) | — | 0.3 |
| Sorbitol 70%, in water | — | 14.0 |

Example 21

Sugar-Free Chewing Gum

The chewing gum base K1 comprised 2.0% butyl rubber (isobutene-isoprene copolymer, MW 400000), 6.0% polyisobutene (MW=43800), 43.5% polyvinyl acetate (MW=12000), 31.5% polyvinyl acetate (MW=47000), 6.75% triacetine and 10.25% calcium carbonate. Production of the chewing gum base K1 and of the chewing gum can take place by analogy to U.S. Pat. No. 5,601,858.

| | I (wt. %) | II (wt. %) | III (wt. %) |
|---|---|---|---|
| Chewing gum base K1 | 26.00 | 27.00 | 26.00 |
| Triacetine | 0.25 | 0.25 | 0.25 |
| Lecithin | 0.50 | 0.50 | 0.50 |
| Sorbitol, crystalline | To 100 | To 100 | To 100 |
| Mannitol | 15.30 | 15.20 | 15.10 |
| Glycerin | 12.10 | 12.00 | 11.80 |
| Saccharin-Na | 0.17 | — | 0.10 |
| Encapsulated aspartame | 1.08 | 1.18 | 1.08 |
| Amorphous silica | 1.00 | 1.00 | 1.00 |
| Cottonseed oil | 0.50 | 0.50 | 0.50 |
| Polyoxyethylene sorbitan monolaurate (E-432) | 1.00 | 1.00 | 1.00 |
| Encapsulated I-carvone (Loading: 30%) | — | 0.20 | — |
| Wintergreen flavor (Example 7.2) | 1.00 | — | 1.70 |
| Eucalyptus menthol type flavor (Example 2.2) | 0.50 | 1.40 | — |
| L-menthyl-L-lactate | — | — | 0.20 |

Example 22

Sugar-free Chewing Gum

The chewing gum base K2 consisted of 28.5% terpene resin, 33.9% polyvinyl acetate (MW=14000), 16.25% hydrogenated vegetable oil, 5.5% mono- and diglycerides, 0.5% polyisobutene (MW 75000), 2.0% butyl rubber (isobutene-isoprene copolymer), 4.6% amorphous silicon dioxide (water content approximately 2.5%), 0.05% antioxidant tert.-butylhydroxytoluol (BHT), 0.2% lecithin, and 8.5% calcium carbonate. Production of the chewing gum base K2 and of the chewing gum can take place by analogy to U.S. Pat. No. 6,986,907.

| | I (wt. %) | II (wt. %) | III (wt. %) |
|---|---|---|---|
| Chewing gum base K2 | 25.30 | 27.30 | 26.30 |
| Sorbitol | To 100 | To 100 | To 100 |
| Glycerin | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.68 |
| Menthol, spray-dried (loading: 25%) | 0.50 | — | 0.50 |
| Cherry flavor, spray-dried (contains benzaldehyde) | — | 1.00 | — |
| Eucalyptus menthol type flavor (Example 2.2); spray dried, flavor content 30% | 1.50 | 1.70 | — |
| Menthol cinnamon type flavor (Example 4) | 1.00 | — | 1.50 |

The chewing gums of recipes (I) and (II) were produced as strips, and that of recipe (III) in pillow shaped compactates and then coated with xylitol.

Example 23

Sugar-free 'Hardboiled Candy'

| Ingredient | I (wt. %) | II (wt. %) |
|---|---|---|
| Water | 2.24 | 2.24 |
| Isomaltitol | 94.98 | To 100 |
| Xylitol | 2.40 | 2.40 |
| Sucralose | 0.03 | 0.03 |
| Acesulfame K | 0.050 | 0.050 |
| Citric acid | 0.050 | 0.050 |
| Pellitorine solution PLM (containing 10% pellitorine) | — | 0.0075 |
| Eucalyptus menthol type flavor (Example 2.2) | 0.25 | 0.20 |

Example 24

'Hardboiled Candy'

| Ingredient | I (wt. %) | II (wt. %) |
| --- | --- | --- |
| Water | 2.75 | 2.50 |
| Sugar | 60.1 | To 100 |
| Glucose syrup | 36.9 | 36.0 |
| Maltose | — | 2.00 |
| Palm kernel oil | — | 0.80 |
| Citric acid | — | 0.25 |
| Ginseng extract | — | 0.40 |
| Blue coloring | — | 0.01 |
| Spearmint type flavor (Example 5.2) | 0.25 | 0.35 |

Example 25

Instant Drink Powder

| | (wt. %) |
| --- | --- |
| Sugar (saccharose) | To 100 |
| Citric acid | 11.58 |
| Trisodium citrate | 0.70 |
| Tricalcium phosphate | 0.60 |
| Vitamin C | 0.66 |
| Grindsted ® JU 543 stabilizer system (Danisco) | 0.90 |
| Saccharin | 0.561 |
| Lemon flavor, spray-dried | — |
| Orange flavor, spray-dried | 1.85 |
| Menthol cinnamon type flavor (Example 4) spray-dried on maltodextrin (DE 15-19) and gum Arabic, flavor loading 40% | 1.20 |

45 g of this instant drink powder were dissolved in 1000 ml by stirring. The drink obtained had a refreshing, cooling taste of orange, cinnamon and mint.

Example 26

Center-filled Hard Throat Candy with Cinnamon Type Flavor and Cool Cinnamon Type Flavor

| | I (wt. %) | II (wt. %) |
| --- | --- | --- |
| Mixture A (shell) (80% of the candies) | | |
| Sugar (Saccharose) | 58.12 | 49.37 |
| Glucose syrup (solid content 80%) | 41.51 | 49.37 |
| Menthol cinnamon type flavor (Example 4) | 0.17 | 0.25 |
| l-menthol | 0.10 | — |
| Lemon oil | 0.10 | 0.10 |
| Citric acid | — | 0.91 |
| Total: | 100 | 100 |
| Mixture B (centre) (20% of the candies) | | |
| High fructose maize syrup (solid sugar content of 85%, just under 15% water) | 84.355 | 84.36 |
| Glycerin | 15.0 | 15.0 |
| Lecithin | 0.02 | 0.02 |
| Cinnamon oil | — | 0.27 |
| Cinnamon spicy flavor (Example 6.2) | 0.28 | — |
| Capsaicin | 0.025 | — |
| Piperine | 0.05 | 0.05 |
| Vanillyl alcohol-n-butyl ether | — | 0.10 |
| Red coloring as 2.5% aqueous solution | 0.20 | 0.20 |
| Vanillin | 0.07 | — |
| Total | 100 | 100 |

In accordance with the methods described in U.S. Pat. No. 6,432,441 (Example 1 there) and in U.S. Pat. Nos. 5,458,894 or 5,002,791 candies with a viscous liquid center were produced. The two mixtures A and B were processed separately into bases for shell (mixture A) or center (mixture B). When consumed by afflicted persons the center-filled candies obtained by means of co-extrusion worked against coughs, sore throats and hoarseness.

The addition of sharp tasting substances (capsaicin, piperine) here took place in order to generate a(n incompletely masking) sharp note.

Example 27

Gelatin Capsules Suitable for Direct Consumption

| | (wt. %) |
| --- | --- |
| Gelatin shell: | |
| Glycerin | 2.014 |
| Gelatin 240 bloom | 7.91 |
| Aspartame | — |
| Sucralose | 0.070 |
| Allura Red (red coloring) | 0.006 |
| Brillant Blue (blue coloring) | 0.005 |
| Center composition: | |
| Vegetable oil triglycerides (coconut oil fraction) | To 100 |
| Flavor G* | 7.5 |
| *Eucalyptus* menthol type flavor (Example 2.2) | 18.5 |

Here flavor G* had the following composition (figures in each case in wt. % in relation to the overall weight of the flavor): 0.1% neotame powder, 29.3% peppermint oil, *Mentha arvensis*, rectified, to 100% peppermint oil, *Mentha piperita*, Willamette type, 2.27% sucralose, 0.7% clove bud oil, 2.28% triacetine, 5.4% diethyl tartrate, 12.1% peppermint oil yakima, 0.7% ethanol, 3.36% 2-hydroxyethylmenthyl carbonate, 2.6% 2-hydroxypropylmenthyl carbonate, 5.77% D-limonene, 5.67% L-menthyl acetate, 0.4% vitamin E-acetate.

The gelatin capsules suitable for direct consumption were produced according to WO 2004/050069 and had a diameter of 5 mm; the weight ratio of center material to shell material was 90:10. The capsules in each case came open in the mouth within less than 10 seconds and dissolved completely within less than 50 seconds.

The invention claimed is:

1. A flavoring agent composition, wherein the flavoring agent composition comprises:
   (a) menthol;
   (b) a quantity of menthane carboxylic acid-N-(4-methoxyphenyl)-amide (WS-12) sufficient to mask the bitterness of the menthol; and
   (c) a quantity of menthone sufficient to solubilize the menthane carboxylic acid-N-(4-methoxyphenyl)-amide (WS-12) so that it masks the bitterness of the menthol without the need for further flavoring agents having a log-$K_{ow}$ value in a range of 1.5-5.

2. A finished product comprising the flavoring agent composition of claim 1, wherein the finished product is selected from the group consisting of a toothpaste, a tooth crème, a tooth cleaning gel, a tooth powder, a mouthwash or mouthwash concentrate, a tooth crème and mouthwash 2-in-1 product, a chewing gum, a hardboiled candy, an instant drink powder, and a gelatin capsule.

3. The finished product according to claim 2, wherein the finished product is a toothpaste, a tooth crème, a tooth cleaning gel, or a tooth powder, and wherein the finished product further comprises cleaning granules.

4. The finished product according to claim 3 further comprising:
(a) 0-10 wt. % of a chewing gum base, in relation to an overall weight of the finished product; and/or
(b) at least one elastomer in an overall quantity of 0-20 wt. %, in relation to the overall weight of the finished product.

5. The finished product according to claim 3 further comprising:
sugar substitutes;
humectants;
thickening agents;
at least one surfactant;
at least one antimicrobial agent;
at least one coloring;
at least one anticaries agent; and/or
at least one further physiological cooling agent, and
wherein the finished product is free from saccharose, glucose and fructose.

6. The finished product according to claim 3, wherein a weight ratio of menthane carboxylic acid-N-(4-methoxyphenyl)-amide (WS-12) to menthol is in a range of 1:5-1:1000.

7. The finished product according to claim 6, wherein the weight ratio of menthane carboxylic acid-N-(4-methoxyphenyl)-amide (WS-12) to an overall quantity, by weight, of menthone is in a range of 1:10-1:200.

8. The finished product according to claim 3, wherein an overall proportion of menthane carboxylic acid-N-(4-methoxyphenyl)-amide (WS-12) is in a range of 0.00015-0.26 wt. % in relation to an overall weight of the finished product.

9. The finished product according to claim 3, wherein the flavoring agent composition comprises:
a) 0.15-1.3 wt. % menthol;
b) 0.00015-0.26 wt. % menthane carboxylic acid-N-(4-methoxyphenyl)-amide (WS-12), wherein a weight ratio of menthane carboxylic acid-N-(4-methoxyphenyl)-amide (WS-12) to menthol is in a range of 1:5-1:1000; and c) menthone, wherein the weight ratio of menthane carboxylic acid-N-(4-methoxyphenyl)-amide (WS-12) to menthone, is a maximum of 1:10,
wherein the wt. % refers to an overall weight of the finished product.

10. A method for masking the bitterness of menthol in a finished product according to claim 3 comprising mixing:
a) menthol,
b) a quantity of menthane carboxylic acid-N-(4-methoxyphenyl)-amide (WS-12), wherein the quantity of menthane carboxylic acid-N-(4-methoxyphenyl)-amide masks the bitterness of the menthol,
c) menthone in an amount such that the solubility of the menthane carboxylic acid-N-(4-methoxyphenyl)-amide (WS-12) is increased, and
d) at least one further teeth cleaning component.

11. The finished product according to claim 2, wherein the finished product is a hardboiled candy.

12. The finished product according to claim 11, wherein the hardboiled candy is sugar-free, and further comprises a sugar substitute selected from the group consisting of isomaltitol (E 953), lactitol (E 966), maltitol, mannitol (E 421), sorbitol (E 420), xylitol (E 967), and mixtures thereof, and/or further comprises an artificial sweetener selected from the group consisting of acesulfame-K, aspartame, cyclamate, a cyclamate salt, neohesperidine dihydrochalcone, sucralose, a sucralose salt, saccharin, and a saccharin salt.

13. The finished product according to claim 11, further comprising a pellitorine solution, wherein the pellitorine solution comprises pellitorine, propylene glycol, and natural peppermint oil.

14. The finished product according to claim 2, wherein the finished product is a chewing gum that further comprises a gum base, and optionally comprises an emulsifier selected from the group consisting of sodium lauryl sulfate, sodium lauryl sarcosinate and cocamidopropyl betaine.

15. The finished product according to claim 14, wherein the chewing gum is sugar-free and further comprises a sugar substitute selected from the group consisting of isomaltitol (E 953), lactitol (E 966), maltitol, mannitol (E 421), sorbitol (E 420), xylitol (E 967) and mixtures thereof, and/or further comprises an artificial sweetener selected from the group consisting of alitame, neotame, thaumatin, acesulfame-K, aspartame, cyclamate, a cyclamate salt, neohesperidine dihydrochalcone, sucralose, a sucralose salt, saccharin, and a saccharin salt.

16. The finished product according to claim 14, further comprising a pellitorine solution, wherein the pellitorine solution comprises pellitorine, propylene glycol, and natural peppermint oil.

* * * * *